(12) United States Patent
Mier et al.

(10) Patent No.: US 9,868,768 B2
(45) Date of Patent: *Jan. 16, 2018

(54) HYDROPHOBIC MODIFIED PRES-DERIVED PEPTIDES OF HEPATITIS B VIRUS (HBV) AND THEIR USE AS VEHICLES FOR THE SPECIFIC DELIVERY OF COMPOUNDS TO THE LIVER

(75) Inventors: Walter Mier, Bensheim (DE); Uwe Haberkorn, Schwetzingen (DE); Stephan Urban, Neustadt (DE)

(73) Assignee: RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 942 days.

This patent is subject to a terminal disclaimer.

(21) Appl. No.: 12/864,197

(22) PCT Filed: Jan. 26, 2009

(86) PCT No.: PCT/EP2009/000477
§ 371 (c)(1),
(2), (4) Date: Oct. 11, 2010

(87) PCT Pub. No.: WO2009/092612
PCT Pub. Date: Jul. 30, 2009

(65) Prior Publication Data
US 2011/0027183 A1   Feb. 3, 2011

Related U.S. Application Data

(60) Provisional application No. 61/062,347, filed on Jan. 25, 2008.

(51) Int. Cl.
| | | |
|---|---|---|
| *A61K 31/7052* | (2006.01) | |
| *C12N 15/63* | (2006.01) | |
| *G01N 33/53* | (2006.01) | |
| *C07K 14/005* | (2006.01) | |
| *A61K 38/16* | (2006.01) | |
| *A61K 39/00* | (2006.01) | |

(52) U.S. Cl.
CPC .......... *C07K 14/005* (2013.01); *A61K 38/162* (2013.01); *A61K 2039/6075* (2013.01); *C07K 2319/033* (2013.01); *C12N 2730/10122* (2013.01); *C12N 2810/6036* (2013.01)

(58) Field of Classification Search
CPC .............................. A61K 39/385; A61K 39/12
See application file for complete search history.

(56) References Cited

U.S. PATENT DOCUMENTS

| | | | | |
|---|---|---|---|---|
| 5,204,096 A | * | 4/1993 | Neurath ............... | A61K 9/1271 424/189.1 |
| 7,892,754 B2 | * | 2/2011 | Gripon ................. | C07K 14/005 424/184.1 |
| 2007/0116721 A1 | * | 5/2007 | Gripon et al. ............. | 424/204.1 |
| 2011/0257080 A1 | * | 10/2011 | Chai et al. .................... | 514/3.7 |

FOREIGN PATENT DOCUMENTS

| | | |
|---|---|---|
| CN | 101045156 A | 10/2007 |
| WO | WO 03/012107 A1 | 2/2003 |

OTHER PUBLICATIONS

Petersen (Journal of Hepatology, Apr. 2006, p. 16 in IDS on Oct. 19, 2010).*
Gripon et al. (Journal of Virology, 2005, vol. 79, p. 1613-1622 in IDS on Oct. 19, 2010).*
Qiuroga et al. (Hepatology, 1990, p. 661-663).*
Glebe, D., et al., "Mapping of the Hepatitis B Virus Attachment Site by Use of Infection-Inhibiting preS1 Lipopeptides and Tupaia Hepatocytes," *Gastroenterology*, Jul. 1, 2005, pp. 234-245, vol. 129, No. 1.
Gripon, P., et al., "Efficient Inhibition of Hepatitis B Virus Infection by Acylated Peptides Derived from the Large Viral Surface Protein," *Journal of Virology*, Feb. 1, 2005, pp. 1613-1622, vol. 79, No. 3.
Petersen, J. et al., "In vivo inhibition of HBV infection by acylated pres peptides in the urokinase-type plasminogen activator (UPA) mouse model," *Journal of Hepatology*, Apr. 1, 2006, pp. S16, vol. 44.
Petersen, J. et al., "Prevention of hepatitis B virus infection in vivo by entry inhibitors derived from the large envelop protein," *Nature Biotechnology*, Feb. 24, 2008, pp. 335-341, vol. 26, No. 3.
Liu, H., "Special target medicine and its use," *Database WPI*, Oct. 7, 2007, Abstract Only.
Neurath, A.R., et al., "Hepatitis B virus surface antigen (HBsAg) as carrier for synthetic peptides having an attached hydrophobic tail," *Molecular Immunology*, Jan. 1, 1989, pp. 53-62, vol. 26, No. 1.

* cited by examiner

*Primary Examiner* — Agnieszka Boesen
(74) *Attorney, Agent, or Firm* — Saliwanchik, Lloyd & Eisenschenk

(57) ABSTRACT

The present invention relates to hydrophobic modified preS-derived peptides of hepatitis B virus (HBV) which are versatile vehicles for the specific delivery of compounds to the liver, preferably to hepatocytes, in vitro as well as in vivo. Any kind of compound, but in particular drugs, such as interferons, viral reverse transcriptase inhibitors or core assembly inhibitors, and/or labels can be specifically targeted to the liver and so be enriched in the liver. This liver targeting can further be used for the targeted diagnosis, prevention and/or treatment of liver diseases or disorders, such as hepatitis, malaria, hepatocellular carcinoma (HCC), as well as for the prevention of HAV, HBV, HCV and/or HDV infection. The present invention relates to pharmaceutical compositions comprising said hydrophobic modified preS-derived peptide(s) and the compound(s) to be specifically delivered to the liver. The present invention furthermore relates to a method for the combined treatment of a liver disease and the prevention of HAV, HBV, HCV and/or HDV infection. The present invention relates also to the use of the preS-derived peptides in gene therapy and the delivery of immunogenic epitopes for hepatocyte-mediated antigen presentation to activate liver-directed immunological responses.

20 Claims, 19 Drawing Sheets

Figure 3
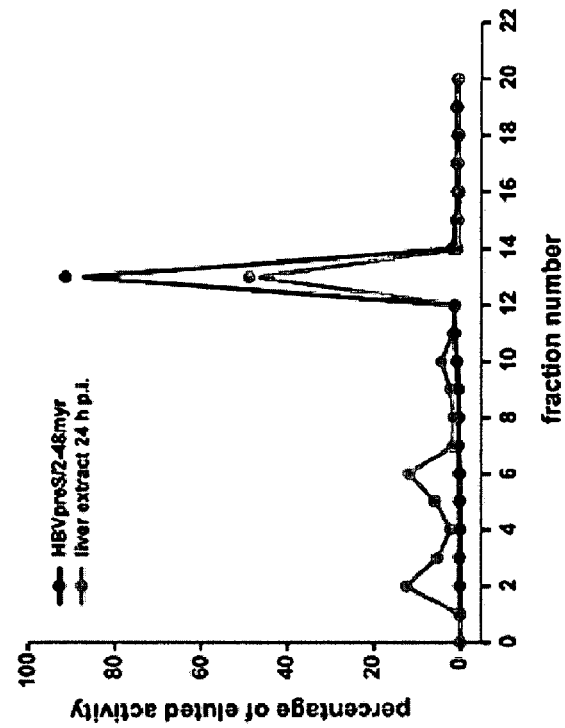
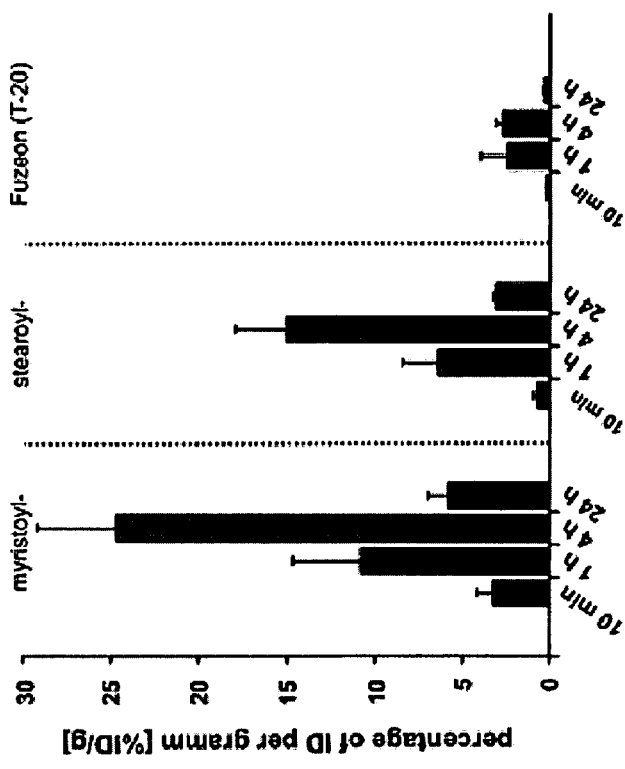

Figure 7
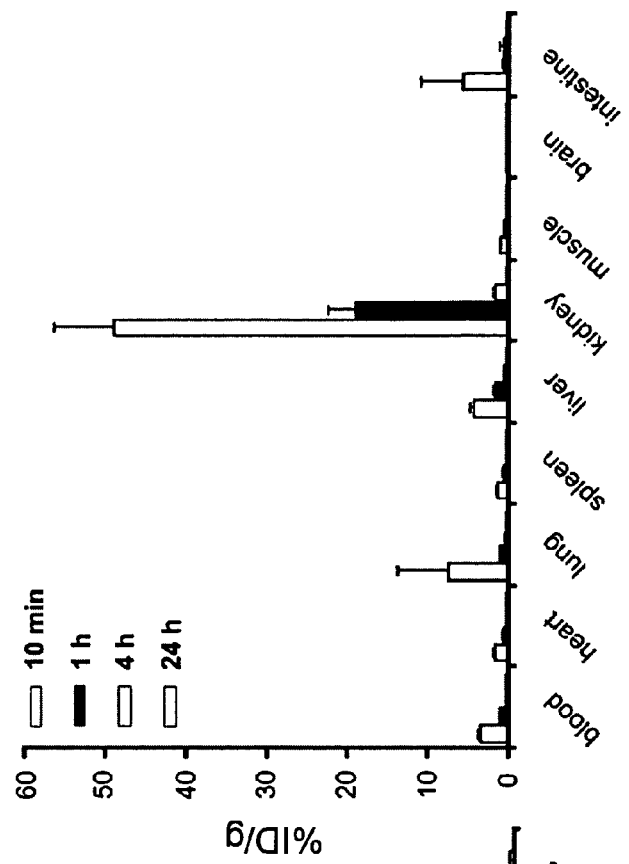
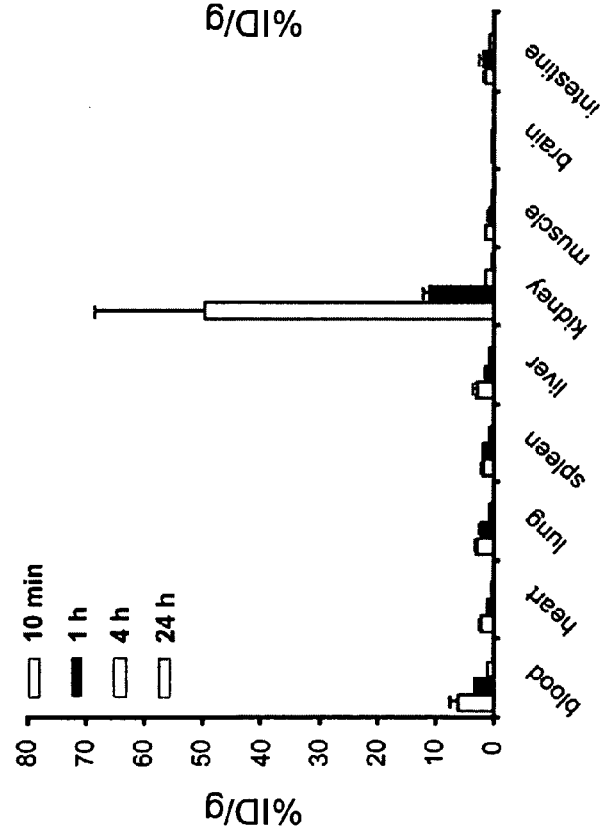

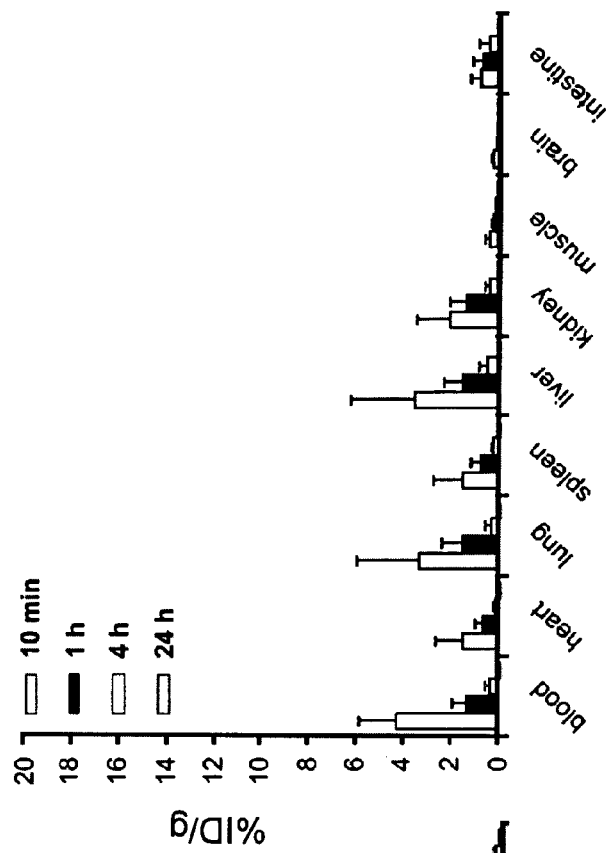
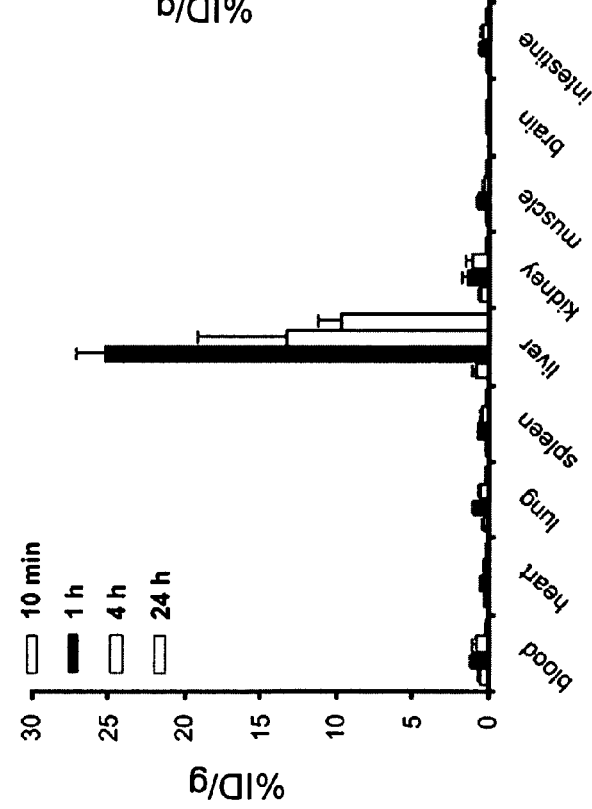
Figure 7

HYDROPHOBIC MODIFIED PRES-DERIVED PEPTIDES OF HEPATITIS B VIRUS (HBV) AND THEIR USE AS VEHICLES FOR THE SPECIFIC DELIVERY OF COMPOUNDS TO THE LIVER

CROSS REFERENCE TO A RELATED APPLICATION

This application is a National Stage Application of International Application Number PCT/EP2009/000477, filed Jan. 26, 2009; which claims the benefit of U.S. Provisional Application Ser. No. 61/062,347, filed Jan. 25, 2008; which are incorporated herein by reference in their entirety.

The present invention relates to hydrophobic modified preS-derived peptides of hepatitis B virus (HBV) which are versatile vehicles for the specific delivery of compounds to the liver, preferably to hepatocytes, in vitro as well as in vivo. Any kind of compound, but in particular drugs, such as interferons, viral reverse transcriptase inhibitors or core assembly inhibitors, and/or labels can be specifically targeted to the liver and so be enriched in the liver. This liver targeting can further be used for the targeted diagnosis, prevention and/or treatment of liver diseases or disorders, such as hepatitis, malaria, hepatocellular carcinoma (HCC), as well as for the prevention of HAV, HBV, HCV and/or HDV infection. The present invention relates to pharmaceutical compositions comprising said hydrophobic modified preS-derived peptide(s) and the compound(s) to be specifically delivered to the liver. The present invention furthermore relates to a method for the combined treatment of a liver disease and the prevention of HAV, HBV, HCV and/or HDV infection. The present invention relates also to the use of the preS-derived peptides in gene therapy and the delivery of immunogenic epitopes for hepatocyte-mediated antigen presentation to activate liver-directed immunological responses.

BACKGROUND OF THE INVENTION

The liver, an organ which is present in vertebrates and other animals, plays a major role in the metabolism and has a number of functions in the body, including glycogen storage, decomposition of red blood cells, synthesis of plasma proteins, and detoxification. The liver also is the largest gland in the human body. It lies below the diaphragm in the thoracic region of the abdomen. It produces bile, an alkaline compound which aids in digestion, via the emulsification of lipids. It also performs and regulates a wide variety of high-volume biochemical reactions requiring specialized tissues.

Hepatocytes make up 70 to 80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile.

There is a wide number of known liver diseases, such as:
Hepatitis: inflammation of the liver, caused mainly by various viruses but also by certain poisons, autoimmunity or hereditary conditions;
Cirrhosis: the formation of fibrous tissue in the liver, replacing dead liver cells. The death of the liver cells can for example be caused by viral hepatitis, alcoholism or contact with other liver-toxic chemicals;
Haemochromatosis: a hereditary disease causing the accumulation of iron in the body, eventually leading to liver damage;
Cancer of the liver: primary hepatocellular carcinoma (HCC) or cholangiocarcinoma and metastatic cancers, usually from other parts of the gastrointestinal tract;
Wilson's disease: a hereditary disease which causes the body to retain copper;
Primary sclerosing cholangitis: an inflammatory disease of the bile duct, autoimmune in nature;
Primary biliary cirrhosis: autoimmune disease of small bile ducts;
Budd-Chiari syndrome: obstruction of the hepatic vein;
Gilbert's syndrome: a genetic disorder of bilirubin metabolism, found in about 5% of the population;
Glycogen storage disease type II: the build-up of glycogen causes progressive muscle weakness (myopathy) throughout the body and affects various body tissues, particularly in the heart, skeletal muscles, liver and nervous system.

There are also many pediatric liver disease, such as biliary atresia, alpha-1-antitrypsin deficiency, alagille syndrome, and progressive familial intrahepatic cholestasis; as well as metabolic diseases.

Furthermore, several pathogens and parasites, especially of tropical diseases, have a liver stage during their life cycle.

For instance malaria, which is one of the most common infectious diseases and an enormous public-health problem. Malaria is caused by protozoan parasites of the genus *Plasmodium*.

The most serious forms of the disease are caused by *Plasmodium falciparum* and *Plasmodium vivax*, but other related species (*Plasmodium ovale, Plasmodium malariae*, and sometimes *Plasmodium knowlesi*) can also infect humans. This group of human-pathogenic *Plasmodium* species is usually referred to as malaria parasites. Malaria parasites are transmitted by female *Anopheles* mosquitoes. Malaria in humans develops via two phases: an exoerythrocytic (hepatic phase or "liver stage") and an erythrocytic phase. When an infected mosquito pierces a person's skin to take a blood meal, sporozoites in the mosquito's saliva enter the bloodstream and migrate to the liver. Within about 30 minutes of being introduced into the human host, they infect hepatocytes, multiplying asexually and asymptomatically for a period of 6-15 days. Once in the liver these organisms differentiate to yield thousands of merozoites which, following rupture of their host cells, escape into the blood and infect red blood cells, thus beginning the erythrocytic stage of the life cycle. The parasite escapes from the liver undetected by wrapping itself in the cell membrane of the infected host liver cell. The parasite is relatively protected from attack by the body's immune system because for most of its human life cycle it resides within the liver and blood cells and is relatively invisible to immune surveillance. There is increasing interest in developing drugs that specifically address the liver specific stages of malaria parasites (e.g. primaquin) in order to obviate the development of blood stages.

Another example is schistosomiasis or bilharziosis, which is a parasitic disease caused by several species of flatworm. Although it has a low mortality rate, schistosomiasis can be very debilitating. It is an often chronic illness that results from infection of the blood with a parasitic flatworm (schistosome). It causes debilitation and causes liver and intestinal damage. It is most commonly found in Asia, Africa, and South America, especially in areas with water that is contaminated with fresh water snails, which contain the parasite.

Hepatitis B virus (HBV), the cause for hepatitis B, is the prototype of a family of small, enveloped DNA viruses of mammals and birds (1). The HBV envelope encloses three proteins termed L—(large), M—(middle) and S—(small) (FIG. 1A). They share the C-terminal S-domain with four transmembrane regions. The M- and L-protein carry additional N-terminal extensions of 55 and, genotype-dependent, 107 or 118 aa (preS2- and preS1) (FIG. 1B). In virions the stoichiometric ratio of L, M and S is about 1:1:4, while the more abundantly secreted non-infectious subviral particles (SVPs) contain almost exclusively S- and only traces of L-protein (2). During synthesis, the preS1-domain of L is myristoylated and at some point of the HBV life cycle translocated through the ER-derived membrane. This modification is essential for infectivity (3,4). HBV as well as the other hepatotropic viruses have a liver tropism, i.e. the liver is the tissue which specifically supports the growth of HBV.

The specific targeting of drugs aims at improving the efficacy of therapies. In 1906 Paul Ehrlich introduced the expression "magic bullet" for the search of optimized treatment strategies. Since then, research in the sense of drug targeting has focused on the development of carrier systems that increase the therapeutic concentration of a drug in target tissue such as tumors or pathogens and thus lowers the side effects for the organism as a whole. Ideally, drug targeting should fulfill the following criteria: 1) exclusive transfer of the drug to the required site of action; 2) a minimum of effects for the remaining organism; 3) use of a pharmacologically inactive vector.

In order to carry a drug to a specific tissue different strategies are pursued. These are for example the use of prodrugs, from which the pharmacologically active part is released in the target tissue by tissue-specific enzymes. A further possibility is to couple effective, non-tissue-specific drugs to tissue-specific, but pharmacologically inert carrier systems like receptor-affine peptides or colloidal particles.

Various drug carriers have been used to enhance liver targeting of drugs. A straightforward approach is based on the active phagocytosis of the reticuloendothelial system in the liver by delivering drugs in particular carriers, such as liposomes and microspheres. For example, it has been shown that following i.v. injection, particulate carriers incorporating a drug are mainly captured by the reticuloendothelial system in the liver, resulting in drug targeting of the liver (5). On the other hand, liver targeting of drugs with positively charged, water-soluble polymers is based on free extravasation of most water-soluble substances from the vascular system of the liver as well as on negative charges on the liver cell surface (6). Thus, polymers have been used as the carrier to allow drugs to target to the liver based on such anatomical and biochemical characteristics of the liver. More specific drug targeting of the liver has been attempted by using asialoglycoprotein receptors of liver cells. The asialoglycoprotein receptor (galactose receptor) is present on hepatocytes with high density. In addition, once a ligand binds to the galactose receptor, the ligand-receptor complex is internalized which allows the cellular uptake of galactosylated ligands (7).

U.S. Pat. No. 7,001,760 B2 disclose recombinant vectors derived from hepatitis B virus (HBV), which can be used for gene therapy, such as the delivery of therapeutic genes to liver cells and the expression of heterologous genes in liver cells. However, HBV vectors have a limited capacity for packaging genes.

However, so far there exist no universal diagnostic, therapeutic and/or preventative approaches that specifically target the organ liver in an animal or bird, in particular a human, and, at the same time, specifically deliver a desired compound or drug to the liver.

Thus, there is the need for universal diagnostic, therapeutic and/or preventative approaches that in a subject specifically target the organ liver and specifically deliver a desired compound or drug to the liver Furthermore, there exist no universal diagnostic, therapeutic and/or preventative approaches that in a subject specifically target the organ liver and specifically deliver a desired compound or drug to the liver as well as, at the same time, prevent entry of Hepatitis B and Hepatitis D viruses into hepatocytes Furthermore there is the need for the specific targeting of the liver with antigenic epitopes to trigger the immune system, such as for vaccination.

The present invention, thus, aims to provide means and methods for the effective, specific targeted diagnosis, prevention and/or treatment of liver diseases and the regulation of the liver function.

SUMMARY OF THE INVENTION

According to the present invention this object is solved by providing a hydrophobic modified preS-derived peptide of HBV.

Said hydrophobic modified preS-derived peptide has the general formula:

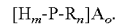

$[H_m\text{-}P\text{-}R_n]A_o$.

P is said preS-derived peptide and comprises the amino acid sequence of the "HBV consensus sequence" or variants thereof.

H is said hydrophobic modification of the preS-derived peptide P, which is N-terminal of P and selected from acylation and addition of hydrophobic moieties; wherein m is at least 1.

R is an optional C-terminal modification (i.e. n is 0 or at least 1) of said preS-derived peptide P.

A is an optional anchor group (i.e. o is 0 or at least 1), which is suitable for the covalent attachment of the compound(s) and is linked to H, P and/or R.

According to the present invention this object is furthermore solved by providing a pharmaceutical composition comprising at least one hydrophobic modified preS-derived peptide of HBV as defined herein and at least a compound to be specifically delivered to the liver, preferably to hepatocytes, as defined herein and optionally a pharmaceutically acceptable carrier and/or excipient.

According to the present invention this object is furthermore solved by using the hydrophobic modified preS-derived peptide(s) of HBV as vehicle or shuttle for the specific delivery of compound(s) to the liver.

According to the present invention this object is furthermore solved by providing the hydrophobic modified preS-derived peptide(s) of HBV or the pharmaceutical composition(s) of the invention for the diagnosis, prevention and/or treatment of a liver disease or disorder or for the regulation of liver function.

According to the present invention this object is furthermore solved by using the hydrophobic modified preS-derived peptide(s) of HBV or the pharmaceutical composition(s) of the invention for the manufacture of a medicament for the diagnosis, prevention and/or treatment of a liver disease or disorder.

According to the present invention this object is furthermore solved by methods for diagnosis, prevention and/or treatment of a liver disease or disorder by utilizing the hydrophobic modified preS-derived peptide(s) of HBV or the pharmaceutical composition(s) of the invention.

According to the present invention this object is furthermore solved by providing a method for the combined diagnosis, prevention and/or treatment of a liver disease or disorder and the prevention of HBV and/or HDV infection by administering to a subject a conjugate as defined herein, which comprises an hydrophobic modified preS-derived peptide of HBV and a compound, or a pharmaceutical composition as defined herein.

According to the present invention this object is furthermore solved by providing the use of a viral vector comprising a nucleic acid encoding a preS-derived peptide P as defined herein for the gene therapy of a liver disease or disorder.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Hydrophobic Modified preS-Derived Peptides of HBV

As outlined above, the present invention provides hydrophobic modified preS-derived peptides of hepatitis B virus (HBV).

The envelope of HBV encloses three proteins termed L (large), M (middle) and S (small) (see FIG. 1A). They share the C-terminal S-domain with four transmembrane regions. The M- and L-protein carry additional N-terminal extensions of 55 and, genotype-dependent, 107 or 118 amino acids (preS2- and preS1) (see FIG. 1B).

Thus, the expression "preS-derived" peptide of HBV according to the present invention refers to a peptide with an amino acid sequence that corresponds to the N-terminal extensions of the L-protein of HBV, preS1, preferably to a consensus sequence of the species and genotypes A to H as well as of woolly monkey (WMHBV), chimpanzee and gorilla hepatitis B viruses, but it also refers to variants thereof, preferably N-terminally and/or C-terminally truncated variants, amino acid substitution variants.

SEQ ID NO. 1 shows the HBV preS consensus amino acid sequence of the species and genotypes A to H as well as of woolly monkey (WMHBV).

See the alignment in FIG. 2 showing the HBV preS consensus sequence (Consensus) and the eight HBV genotypes (A-H) as well as the woolly monkey HBV (WMHBV) preS sequence encompassing amino acids 2-48. Note that the genotypes A, B, C, E, F, G and H have up to eleven additional amino acids at their N-termini.

The amino acid sequence of HBV "genotype C" within this application refers to an artificial sequence, which corresponds to or is identical to the HBV Genotype C, as e.g. shown in Genbank ABV02850.1, except that position 46 (according to the numbering as described below) is Lys (K) in the genotype C of the present invention instead of Gln (Q) as in the Genbank sequence; the HBV genotype C sequence of this application can also be referred to as "HBV genotype C Q46K". See also SEQ ID NOs. 4, 12, 21-27.

FIG. 2 also shows the numbering of the amino acid residues of the HBV preS consensus sequence, which will be referred to throughout this specification:

Amino acid residue number 1 is the methionine (Met1) of genotype D (formerly described as subtype ayw, see also SEQ ID NO. 5), whereas amino acid residue number (−11) is the methionine (Met(−11)) of genotype C (SEQ ID NO. 4). In vivo Met1 or Met(−11), respectively, is cleaved off by a cellular methionyl aminopeptidase and modified by a subsequent transfer of a myristoyl residue from Myristoyl-CoA to amino acid residue number 2 glycine (Gly2) or amino acid residue number (−10) glycine (Gly(−10)), respectively, by N-myristoyl transferase. The N-terminal amino acid residue of genotype D is the natural amino acid Glycin (Gly2) and is numbered 2 according to the respective numbering from the codons of the underlying open reading frame of L (or e.g. Gly(−10) for genotype C).

The HBV preS consensus sequence also comprises the additional N-terminal amino acids of genotypes A, B, C, E, F, G and H (designated at "−" positions). Thus, in total the HBV preS consensus sequence encompasses positions (−11) to 48.

Thus, there is a difference between the above described numbering and the actual listing of amino acids in SEQ ID NO. 1, e.g.

Met (−11), residue number (−11), is listed as amino acid residue 1 in SEQ ID NO. 1;

Gly (−10), residue number (−10), is listed as amino acid residue 2 in SEQ ID NO. 1;

Met 1, residue number 1, is listed as amino acid residue 12 in SEQ ID NO. 1;

Gly 2, residue number 2, is listed as amino acid residue 13 in SEQ ID NO. 1;

Gly 48, residue number 48, is listed as amino acid residue 58 in SEQ ID NO. 1.

```
HBV preS consensus sequence (positions (-11) to 48)
                                          SEQ ID NO: 1
(-11)-M GGWSS TPRKG MGTNL SVPNP LGFFP DHQLD PAFRA

NSNNP DWDFN PNKDH WPEAN KVG-48

HBV Genotype A
                                          SEQ ID NO: 2
(-11)-M GGWSS KPRKG MGTNL SVPNP LGFFP DHQLD PAFGA

NSNNP DWDFN PVKDD WPAAN QVG-48

HBV Genotype B
                                          SEQ ID NO: 3
(-11)-M GGWSS KPRKG MGTNL SVPNP LGFFP DHQLD PAFKA

NSENP DWDLN PHKDN WPDAN KVG-48 artificial amino acid sequence, which corresponds
to HBV Genotype C except that position 46 is Lys
(K) instead of Gln (Q); Q46K
                                          SEQ ID NO: 4
(-11)-M GGWSS KPRQG MGTNL SVPNP LGFFP DHQLD PAFGA

NSNNP DWDFN PNKDH WPEAN KVG-48

HBV Genotype D
```

-continued

SEQ ID NO: 5
1-MGQNL STSNP LGFFP DHQLD PAFRA NTANP DWDFN PNKDT

WPDAN KVG-48

HBV Genotype E
SEQ ID NO: 6
(-10)-MGLSW TVPLE WGKNI STTNP LGFFP DHQLD PAFRA

NTRNP DWDHN PNKDH WTEAN KVG-48

HBV Genotype F
SEQ ID NO: 7
(-11)-M GAPLS TTRRG MGQNL SVPNP LGFFP DHQLD PLFRA

NSSSP DWDFN TNKDS WPMAN KVG-48

HBV Genotype G
SEQ ID NO: 8
(-10)-MGLSW TVPLE WGKNL SASNP LGFLP DHQLD PAFRA

NTNNP DWDFN PKKDP WPEAN KVG-48

HBV Genotype H
SEQ ID NO: 9
(-11)-M GAPLS TARRG MGQNL SVPNP LGFFP DHQLD PLFRA

NSSSP DWDFN TNKDN WPMAN KVG-48

WMHBV
SEQ ID NO: 10
1-MGLNQ STFNP LGFFP SHQLD PLFKA NAGSA DWDKN PNKDP

WPQAH DTA-48

For SEQ ID NOs. 2-10 see also Genbank Accession numbers:
HBV Genotype A Genbank AAT28684.1
HBV Genotype B Genbank AAU01950.1
HBV Genotype C Genbank ABV02850.1 (wherein position 46 is Lys (K) (as in SEQ ID NO. 4) instead of Gln (Q) (of ABV02850.1)
HBV Genotype D Genbank AAR19337.1
HBV Genotype E Genbank ABS31101.1
HBV Genotype F Genbank ABK19774.1
HBV Genotype G Genbank AAF34735.1/AF160501_3
HBV Genotype H Genbank AAM09052.1
WMHBV Genbank AAC16905.1

A hydrophobic modified preS-derived peptide of HBV according to the present invention has the formula $$[H_m\text{-}P\text{-}R_n]A_o$$

wherein
P is said preS-derived peptide;
H is said hydrophobic modification of P;
R is a C-terminal modification of P;
A is an anchor group;
m is at least 1;
n is 0 or at least 1;
o is 0 or at least 1.
Preferably, not both n and o are 0.

The preS-derived peptide of HBV, P, according to the present invention comprises:
the amino acid sequence of the HBV preS consensus sequence as shown in SEQ ID NO. 1 or
variants thereof.

"Variants" are preferably N-terminally and/or C-terminally truncated variants, amino acid substitution or deletion variants, or prolonged variants. Variants comprise furthermore an amino acid sequence comprising modified amino acid(s), unnatural amino acid(s) or peptidomimetic(s) or further compounds which can mimic a peptide backbone/structure.

Preferably, variants are selected from N-terminally and/or C-terminally truncated variants of SEQ ID NO. 1; amino acid substitution or deletion variants; variants comprising modified amino acid(s), unnatural amino acid(s) or peptidomimetic(s) or further compounds which can mimic a peptide backbone/structure.

According to the invention, a variant of a hydrophobic modified preS-derived peptide contains at least 10 or 20 consecutive amino acids of SEQ ID NO. 1 and can consist of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acids of SEQ ID NO. 1 or its variants.

N-terminally and/or C-terminally truncated variants comprise preferably at least 14 consecutive amino acids (such as residues 5 to 18), more preferably at least 19 consecutive amino acids (such as residues 2 to 20), even more preferably at least 20 consecutive amino acids of SEQ ID NO. 1 (such as residues 2 to 21).

The term "variant" also refers to the homologous sequences found in the different viral species, strains or subtypes of the hepadnavirus genus, such as HBV strain alpha1, HBV strain LSH (chimpanzee isolate), woolly monkey HBV (WMHBV), or strains selected from the group consisting of the HBV genotypes A to H, as well as the HBV genotype C as defined herein, Q46K (such as SEQ ID NO. 4).

The term "variant" also refers to homologous sequences which show at least 50% sequence identity to SEQ ID NO. 1 or any other amino acid sequence disclosed herein, preferably 70%, more preferably 80%, even more preferably 90% or 95%.

Thus, in preferred hydrophobic modified preS-derived peptide according to the invention P comprises a variant of SEQ ID NO. 1 with an amino acid sequence of the different viral species, strains or subtypes, preferably of the genotypes of HBV or woolly monkey HBV (WMHBV) or variants thereof.

Preferably, P comprises an amino acid sequence selected from SEQ ID NOs. 2 to 10 or variants thereof (see also FIG. 2).

In a preferred embodiment in the hydrophobic modified preS-derived peptides according to the invention P comprises a variant of SEQ ID NO. 1 with an amino acid sequence selected from
amino acid residues 2 to 48 [SEQ ID NO. 11]
amino acid residues 2 to 20
amino acid residues 2 to 21 [SEQ ID NO. 12]
amino acid residues 9 to 15 [SEQ ID NO. 21]
of the HBV preS consensus sequence as shown in SEQ ID NO. 1.

More preferably, P does not comprise amino acid substitutions and/or deletions at residues 9 to 22 of SEQ ID NO. 1, such as by deleting residues 17 to 21.

More preferably, P does not comprise amino acid substitutions and/or deletions at residues 9 to 15 of SEQ ID NO. 1.

More preferably, the sequence motif NPLGFFP (corresponding to residues 9 to 15 of SEQ ID NO. 1) is not interrupted or modified, such as by replacing residues 11-15 by D-amino acids.

The inventors have identified these amino acid residues to be important for the liver tropism of the hydrophobic modified preS-derived peptides of HBV, as described below.

More preferably, in the hydrophobic modified preS-derived peptides according to the invention P comprises a variant of SEQ ID NO. 1 with an amino acid sequence selected from
amino acid residues 2 to 48 of the consensus sequence [SEQ ID NO. 11];
amino acid residues 2 to 21 of the consensus sequence [SEQ ID NO. 12];
amino acid residues 2 to 48 of genotype C [SEQ ID NO. 13];
amino acid residues 5 to 48 of genotype C [SEQ ID NO. 14];
amino acid residues 9 to 48 of genotype C [SEQ ID NO. 15];
amino acid residues 2 to 21 of genotype C [SEQ ID NO. 16];
amino acid residues 5 to 21 of genotype C [SEQ ID NO. 17];
amino acid residues 9 to 21 of genotype C [SEQ ID NO. 18];
amino acid residues 2 to 15 of genotype C [SEQ ID NO. 19];
amino acid residues 5 to 15 of genotype C [SEQ ID NO. 20];
amino acid residues 9 to 15 of genotype C [SEQ ID NO. 21];
amino acid residues 2 to 48 of genotype D [SEQ ID NO. 23];
amino acid residues 5 to 48 of genotype D [SEQ ID NO. 24];
amino acid residues 9 to 48 of genotype D [SEQ ID NO. 25];
amino acid residues 2 to 21 of genotype D [SEQ ID NO. 26];
amino acid residues 5 to 21 of genotype D [SEQ ID NO. 27];
amino acid residues 9 to 21 of genotype D [SEQ ID NO. 28];
amino acid residues 2 to 20 of genotype D [SEQ ID NO. 38];
amino acid residues 2 to 15 of genotype D [SEQ ID NO. 29];
amino acid residues 5 to 15 of genotype D [SEQ ID NO. 30];
amino acid residues 9 to 15 of genotype D [SEQ ID NO. 21].

Thus preferably, P comprises an amino acid sequence selected from SEQ ID NOs. 11 to 30 and 38 or variants thereof.

"Variants" of SEQ ID NO. 1 also comprise variants or "analogues" comprising amino acid deletions, amino acid substitutions, such as conservative or non conservative replacement by other amino acids or by isosteres (modified amino acids that bear close structural and spatial similarity to protein amino acids), amino acid additions or isostere additions, as long as the sequence still shows liver tropism, preferably more than 10% of the injected dose/g liver tissue after 1 h.

Conservative amino acid substitutions typically relate to substitutions among amino acids of the same class. These classes include, for example,
amino acids having uncharged polar side chains, such as asparagine, glutamine, serine, threonine and tyrosine;
amino acids having basic side chains, such as lysine, arginine, and histidine;
amino acids having acidic side chains, such as aspartic acid and glutamic acid; and
amino acids having nonpolar side chains, such as glycine, alanine, valine, leucine, isoleucine, proline, phenylalanine, methionine, tryptophan, and cysteine.

Preferably, the hydrophobic modified preS-derived peptides of the invention are modified to decrease their immunogenic properties.

Thus, preferred sequence motifs to be modified by substitution and/or deletion are sequences responsible for the immunogenicity, such as B-cell epitopes and/or T-cell epitopes.

B-cell epitopes of HBV are preferably amino acid residues 20 to 23, motif DPAF, of SEQ ID NO. 1 and amino acid residues 26 to 32, motif NSNNPDW of the consensus sequence (SEQ ID NO. 1) and genotype C (SEQ ID NO. 4) or NTANPDW of genotype D (SEQ ID NO. 5).

In a preferred embodiment amino acid residues 20 to 23 of SEQ ID NO. 1 are modified, preferably by amino acid substitution, and/or the amino acid residues 26 to 32 are modified, preferably by amino acid substitution.

Preferably, amino acid residues 20 to 23 of SEQ ID NO. 1 (motif DPAF) are modified by alanine amino acid substitution, preferably into motif APAF.

Preferably, amino acid residues 26 to 32 of SEQ ID NO. 1 are modified by alanine amino acid substitution, preferably into motif NANAPDW or NAAAPDW.

Further preferred sequence motifs to be modified by substitution and/or deletion are sequences that are antibody recognition motifs.

A preferred objective for modifying sequences responsible for the immunogenicity, such as B-cell epitopes, is decreasing the immunogenicity of the hydrophobic modified preS-derived peptides of the invention. The person of skill in the art is aware of this objective and its advantages and disadvantages. Importantly, while decreasing the immunogenicity of the hydrophobic modified preS-derived peptides of the invention one has also to consider the desired liver targeting/tropism feature. Shuttle peptides that do not elicit immune responses can be repeatedly administered without systemic removal from humoral immune responses.

Thus, in a preferred embodiment P does not comprise amino acid substitutions and/or deletions at residues 9 to 15 of SEQ ID NO. 1 in order to maintain the liver targeting/tropism.

A more preferred hydrophobic modified preS-derived peptide of this invention shows a high liver targeting/tropism and low or no immunogenicity.

In a preferred embodiment P comprises an amino acid sequence selected from SEQ ID NOs. 31 to 37 or variants thereof.

See also Tables and the respective Figures and Examples.
In a more preferred embodiment P comprises an amino acid sequence selected from
SEQ ID NO. 11 (residues 2 to 48 of the consensus sequence),
SEQ ID NO. 12 (residues 2 to 21 of the consensus sequence),
SEQ ID NO. 13 (residues 2 to 48 of genotype C),
SEQ ID NO. 16 (residues 2 to 21 of genotype C),
SEQ ID NO. 23 (residues 2 to 48 of genotype D),
SEQ ID NO. 26 (residues 2 to 21 of genotype D),
SEQ ID NO. 38 (residues 2 to 20 of genotype D), and
SEQ ID NO. 31 (residues 2 to 48 of genotype C and Ala mutations in positions 21, 23, 29 and 30).

The above are the preferred amino acid sequences which fulfill the preferred combination of the desired features: short amino acid sequence, low or no immunogenicity and efficient liver targeting.

The hydrophobic modification (H) of the preS-derived peptide P is N-terminal of P.

"N-terminal" refers to the hydrophobic modification at the N-terminus, i.e. the respective first amino acid residue (e.g. Gly 2), but comprises also the hydrophobic modification in close proximity to the N-terminus, such as respective amino acid residues (−4), (−3), (−2), (−1), 1, 2 or 3 or 4. Thus, the hydrophobic modification can furthermore be obtained by an attachment of a hydrophobic moiety at a site close to the N-terminus of P.

The hydrophobic modification of said preS-derived peptide of HBV according to the present invention adds a hydrophobic moiety to the peptide.

Furthermore, m is at least 1, i.e. modification with at least one hydrophobic moiety or group.

In preferred embodiments of this invention m is 1, 2, 3, 4 or more. That is, P can be modified with more than one hydrophobic moiety or group, such as 2. The hydrophobic moieties or groups can be the same or different to each other.

The hydrophobic modification of said preS-derived peptide of HBV according to the present invention is selected from:
acylation;
addition of hydrophobic moieties.

Acylation is preferably selected from acylation with carboxylic acids, fatty acids, amino acids with lipophilic side chains.

Preferred fatty acids are saturated or unsaturated fatty acids, branched or unbranched fatty acids, preferably with 8 to 22 carbon atoms (C8 to C22).

More preferably, the hydrophobic modification by acylation is selected from acylation with myristoyl (C14), palmitoyl (C16) or stearoyl (C18).

Modification by myristoylation is preferred in in vivo and medicinal applications due to its higher safety, e.g. not showing the adverse effects of the stearoyl group (innate immune response etc).

The addition of hydrophobic moieties is preferably selected from addition of cholesterol, derivatives of cholesterol, phospholipids, glycolipids, glycerol esters, steroids, ceramids, isoprene derivatives, adamantane, farnesol, aliphatic groups, polyaromatic compounds.

The attachment of the hydrophobic moieties is preferably by covalent binding, which can be achieved via carbamate, amide, ether, disulfide or any other linkage that is within the skill of the person skilled in the art.

Thus, the hydrophobic modified, preferably acylated preS-derived peptides of this invention are preferably lipopeptides due to their N-terminal lipophilic or hydrophobic group/moiety.

The C-terminal modification (R) of said preS-derived peptide P is preferably a modification with a moiety that protects from degradation, such as in vivo degradation.

"C-terminal" refers to the modification at the C-terminus, i.e. the respective last amino acid residue, but comprises also the modification in close proximity to the C-terminus, such as the last but one amino acid residue, the last but two amino acid residue or more amino acid residues (e.g. introduction of one D-amino acid that protects the carrier from enzymatic degradation e.g. by the action of carboxypeptidases).

The skilled artisan will be able to select the respective suitable moiety(s) depending on the respective application.

Preferred moieties that protect from degradation are selected from amides, D-amino acids, modified amino acids, cyclic amino acids, albumin, natural and synthetic polymers, such as PEG, glycane.

Furthermore, n is 0 or at least 1, i.e. the C-terminal modification (R) is optional.

Preferably, n is 1.

In further embodiments of this invention n is 1, 2, 3, 4 or more. That is, the C-terminus of P or its proximity can be modified with more than one moiety or group, such as 2. The moieties or groups can be the same or different to each other.

In an embodiment of this invention H and/or R are linked to P via a linker or spacer.

Linker or spacer are known to the skilled artisan, such as polyalanine, polyglycin, carbohydrates, $(CH_2)_n$ groups.

The skilled artisan will, thus, be able to select the respective suitable linker(s) or spacer(s) depending on the respective application.

The anchor group (A) serves as a point of attachment for a compound, a tag, a label.

In a preferred embodiment, the anchor group is "C-terminal" of P, wherein "C-terminal" refers to the modification at the C-terminus, i.e. the respective last amino acid residue, but comprises also the close proximity of the C-terminus, such as the last but one amino acid residue, the last but two amino acid residue or more amino acid residues. In this case n can be 0, thus there is no other C-terminal modification R.

In this embodiment, the hydrophobic modified preS-derived peptide of HBV can have the following general formula

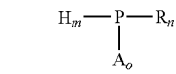

The anchor group A can be at an amino acid side chain of the preS-derived peptide P or can be the amino acid side chain of the preS-derived peptide P itself, i.e. A can be a side chain itself or a modified side chain.

The anchor group can also be a modified amino acid residue which was introduced into the amino acid sequence of P to serve as an anchor group.

In other embodiments of the invention the anchor group A is attached to the hydrophobic modification H and/or the C-terminal modification R.

Preferred anchor groups are selected from ester, ether, disulfide, amide, thiol, thioester.

The skilled artisan will be able to select the respective suitable anchor group(s) depending on the respective compound, tag, label etc. to be attached.

The anchor group can furthermore be suitable for attaching a complex-forming component, such as of the biotin/avidin, polyarginine/oligonucleotide (e.g. siRNA) complex.

Furthermore, o is 0 or at least 1, i.e. the anchor group (R) is optional.

Preferably, o is 1.

In further embodiments of this invention o is 1, 2, 3, 4 or more. That is, there are more than one anchor group, such as 2. The anchor groups can be the same or different to each other, allowing the attachment of several compounds, such as a drug and a label or different drugs.

For preferred hydrophobic modified preS-derived peptides, see also Tables 1 and 2.

More preferred hydrophobic modified preS-derived peptides of the invention are the following:
P comprises an amino acid sequence selected from SEQ ID NO. 11, SEQ ID NO. 12, SEQ ID NO. 13, SEQ ID NO. 16, SEQ ID NO. 23, SEQ ID NO. 26, SEQ ID NO. 31 and SEQ ID NO. 38, and H is a hydrophobic modification by acylation with stearoyl (C18) or myristoyl (C14).

Thus, the more preferred hydrophobic modified preS-derived peptides of the invention are:

| Designation of peptide | Amino acid sequence | Hydrophobic modification |
|---|---|---|
| HBVpreS/2-48$^{stearoyl}$ (consensus) | SEQ ID NO. 11 | Stearoyl (C18) |
| HBVpreS/2-48$^{stearoyl}$ (consensus) | SEQ ID NO. 12 | Stearoyl (C18) |
| HBVpreS/2-48$^{stearoyl}$ (C) | SEQ ID NO. 13 | Stearoyl (C18) |
| HBVpreS/2-48$^{stearoyl}$ (C) | SEQ ID NO. 16 | Stearoyl (C18) |
| HBVpreS/2-48$^{myr}$ (C) | SEQ ID NO. 13 | Myristoyl (C14) |
| HBVpreS/2-48$^{myr}$ (D) | SEQ ID NO. 23 | Myristoyl (C14) |
| HBVpreS/2-21$^{stearoyl}$ (D) | SEQ ID NO. 26 | Stearoyl (C18) |
| HBVpreS/2-20$^{myr}$ (D) | SEQ ID NO. 38 | Myristoyl (C14) |
| HBVpreS/2-48$^{stearoyl}$-Ala$^{21,23,29,30}$ (C) | SEQ ID NO. 31 | Stearoyl (C18) |

Wherein (C) refers to HBV genotype C Q46K.

The peptides of this invention can be prepared by a variety of procedures readily known to those skilled in the art, in general by synthetic chemical procedures and/or genetic engineering procedures.

Synthetic chemical procedures include more particularly the solid phase sequential and block synthesis (Erickson and Merrifield, 1976). The solid phase sequential procedure can be performed using established automated methods such as by use of an automated peptide synthesizer. In this procedure an α-amino protected amino acid is bound to a resin support. The resin support employed can be any suitable resin conventionally employed in the art for the solid phase preparation of (poly)peptides, preferably polystyrene which has been copolymerized with polyoxyethylen to provide sites for ester formation with the initially introduced o-amino protected amino acid. This optimized method, applied by the inventors, has been explicitly described (see e.g. 12). The amino acids are introduced one by one (stepwise). Each synthesis cycle corresponding to the introduction of one amino acid includes a deprotection step, successive washing steps, a coupling step with activation of the amino acid, and subsequent washing steps. Each of these steps is followed by a filtration. The reactive agents for coupling are the classical reactive agents for (poly)peptide synthesis such as dicyclohexylcarbodiimide, hydroxybenzotriazole, benzotriazil-1-yl-oxytris (dimethylamino) phosphonium hexafluorophosphate, and diphenylphosphorylazide. After synthesis of the polypeptide on the resin, the polypeptide is separated from the resin by a treatment with a strong acid such as trifluoroacetic acid in the presence of anisol, ethanedithiol or 2-methylindole. The compound is then purified by the classical techniques of purification, in particular by means of HPLC.

The peptides of the present invention may also be obtained by coupling (poly)peptide fragments that are selectively protected, this coupling being effected e.g. in a solution.

The peptides can further be produced by genetic engineering techniques as known to the skilled artisan. An eukaryotic expression system, such as the baculovirus system, is particularly suitable. According to this procedure proteins are expressed in insect cells infected with a recombinant baculovirus containing a nucleic acid sequence encoding a heterologous protein and regulating nucleic acid sequences, such as a promoter. Several cell-lines are available for infection with recombinant baculovirus, such as cell line Sf-9, available from the American Type Culture Collection (CRL 1711). Expression in prokaryotic expression system, such as E. coli, is also particularly suitable.

The introduction of the hydrophobic moiety to the peptide can be accomplished by a variety of procedures readily known to those skilled in the art, including synthetic and genetic engineering approaches.

Alternatively, the peptides and/or fusion peptides (i.e. hydrophobic modified peptides) can be produced by stably transfected eukaryotic cell lines, like CHO and other cell lines which are known in the art and usually used for generating vaccines and the like. Due to the intrinsic property that the N-terminal 47-preS1 amino acids promote secretion of a myristoylated protein/peptide, the biologically active hydrophobic modified peptide can be extracted from cell culture supernatants.

Vectors and Shuttles for Liver Targeting

As outlined above, the present invention provides the use of the hydrophobic modified preS-derived peptides of HBV as vehicle or shuttle for the specific delivery of a compound to the liver.

"Vehicle" or "shuttle" for the specific delivery of a compound to the liver according to the present invention refers to the liver tropism or hepatotropism of the hydrophobic modified preS-derived peptides of HBV as found by the inventors and described herein, i.e. to their capacity to selectively accumulate in the liver, preferably to selectively accumulate at the plasma membrane of hepatocytes as well as to selectively enter into hepatocytes.

The invention is based on the finding of a highly specific liver accumulation and on the identification of the determinants of the liver tropism of HBV in the preS1 sequence of HBV by the inventors. Thus, the invention uses the knowledge about the determinants of the liver tropism for the design of universal vehicles or shuttles for specific liver targeting or delivery, respectively.

The hydrophobic modified preS-derived peptides of the present invention are versatile vehicles or shuttles for specifically delivering compound(s) to the liver.

Preferably, the specific delivery of a compound to the liver is the specific delivery of the compound to hepatocytes.

Furthermore, the compound can specifically be delivered to hepatocytes in vitro as well as in vivo.

The compound is preferably specifically delivered to the liver of an animal, preferably mammal or human, or a bird.

Compounds to be Delivered

The "compound" to be specifically delivered to the liver according to this invention can be any kind of compound.

Preferred compounds are drugs and/or labels.

Drugs can be in form of prodrugs or preprodrugs.

A compound can also be a virus or derivatives thereof, such as a replication-deficient or a replication-competent recombinant virus (e.g. an Adenovirus or an Adeno-associated virus) that has been chemically or genetically modified to expose the targeting sequence on its surface and is thereby redirected to infect hepatocytes. These viruses shall be applicable for hepatocyte specific gene delivery.

In a preferred embodiment of the invention the compound to be specifically delivered to hepatocytes is a drug (or a drug in form of a prodrug) and is preferably selected from

| Drug class | Examples |
|---|---|
| interferon | IFNα |
| viral reverse transcriptase inhibitor | Lamivudine, Adefovir, Entecavir |
| viral RNA polymerase inhibitor | HCV NS5B polymerase inhibitor |
| viral core assembly inhibitor or | for hepatropic viruses |

| Drug class | Examples |
| --- | --- |
| viral nucleocapsid inhibitor | e.g. dihydroarylpyrimidine-derived HBV capsid assembly inhibitors |
| kinase inhibitor | Raf kinase inhibitor Sorafenib (BAY 43-9006) |
| nucleoside analogue | |
| protease inhibitor - viral or general protease inhibitor | HCV NS3 protease inhibitor, BILN-2061, VX950 |
| proteasom inhibitor | MG132, bortezomib |
| antibody or fragment thereof | Neutralizing anti-HCV E2 antibodies |
| siRNA or precursor thereof | HBV, HCV, HDV-specific siRNAs and modifications thereof; siRNAs targeting other sequences, including cellular sequences |
| farnesylation inhibitor; such as farnesyl transferase inhibitor (FTI) | |
| alcohol dehydrogenase (ADH) or activator thereof | |
| cholesterol biosynthesis inhibitor, such as HMD-CoA-reductase inhibitors | Mevinacor/Lovastatin |
| inhibitor of the liver stage of a virus or a non-viral pathogen, such as malaria, schistosomiasis (bilharziosis), leishmaniasis | Primaquine |
| inhibitors of other viruses that occasionally infect the liver | e.g. Zovirax for the treatment of herpes virus infection |
| antibiotics to specifically act in the liver | |

The compound is preferably selected from a clinically approved drug.

In an embodiment the compound to be delivered is IFN-alpha.

The hydrophobic modified preS1-derived peptide(s) used in such an embodiment can be HBVpreS/2-20$^{myr}$(D), HBVpreS/2-48$^{myr}$(D), HBVpreS/2-20$^{stearoyl}$(D), HBVpreS/2-48$^{stearoyl}$(D) (see also FIG. 14). A fusion protein or construct with mouse interferon-alpha was obtained by recombinant expression in insect cells using the baculovirus expression system.

See also FIGS. 14 and 15 as well as Examples.

In a preferred embodiment of the invention the compound to be specifically delivered to hepatocytes is a label and is preferably selected from a fluorescent dye, a radioisotope and a contrast agent.

Preferred radioisotopes are $^{131}$I, $^{125}$I, $^{99m}$Tc, $^{18}$F, $^{68}$Ga, $^{111}$In, $^{90}$Y, $^{177}$Lu.

Preferred fluorescent dyes are Alexa dyes, derivatives of rhodamine and fluorescein, Cy-dyes, FITC.

Preferred contrast agents are Gadolinium (Gd) complexes, supramagnetic iron (Fe) complexes and particles, compounds containing atoms of high atomic number, i.e. iodine for computer tomography (CT), microbubbles and carriers such as liposomes that contain these contrast agents.

In a further preferred embodiment of the present invention also the compound is labelled, i.e. carries a label as defined herein.

In preferred embodiments the compounds are in form of depots or carriers, which e.g. carry a drug, prodrug or label. Such depots or carriers are known in the art, such as nanoparticles, liposomes, microbubbles, gas emulsions.

In other embodiments of the present invention the compound to be delivered to the liver is selected from immunogenic epitopes. Preferred immunogenic epitopes when delivered to the liver serve hepatocyte-mediated antigen presentation in order to activate liver-directed immunological responses.

In a preferred embodiment the compound and the hydrophobic modified preS-derived peptide of HBV form a conjugate.

Preferably, the conjugate of compound and hydrophobic modified preS-derived peptide is formed by covalent attachment or by complex formation.

Preferably, in a conjugate the compound is covalently attached to the hydrophobic modified preS-derived peptide, preferably by attaching the compound to an anchor group A. The form of attachment depends on the type of compound. The person of skill in the art will be able to determine suitable anchor groups for forming suitable conjugates.

Preferably, A furthermore comprises a spacer or linker.

The spacer or linker preferably comprises a recognition site for hepatocyte specific activation, which is preferably recognized by a liver protein.

The recognition site is preferably a proteolytic cleavage site. The liver protein is, thus, preferably a hepatocellular protein, more preferably a hepatocellular proteolytic enzyme. Thus, the conjugate can be administered to a subject and will be transported through the body, such as in the bodily fluids, without being cleaved. However, as soon as the conjugate reaches its target, the liver or the hepatocytes, respectively, the liver protein, such as a hepatocellular proteolytic enzyme will cleave the proteolytic cleavage site and release the compound from its shuttle, i.e. the hydrophobic modified preS-derived peptide.

Further preferred liver proteins are cytochromes, such as cytochrome P450. The HepDirect® technology (of Metabasis Technologies, Inc.) as used in Adefovir or Pradevofir, is also suitable for the present invention.

In one embodiment the conjugate of compound and hydrophobic modified preS-derived peptide is formed by complex formation. Preferred complexes useful in the invention are biotin/avidin, polyarginine/oligonucleotide (e.g. siRNA). The skilled artisan will be able to determine suitable complex components and to design the compound and hydrophobic modified preS-derived peptide accordingly.

The hydrophobic modified preS-derived peptide, in particular the conjugates of the present invention, are preferably used to enrich a compound, that is shuttled to the liver, in the liver.

Preferably, the compound is cleaved of the conjugate with the hydrophobic modified preS-derived peptide of HBV by a liver protein, preferably a hepatocellular proteolytic enzyme, in particular in vivo in the liver.

Diagnosis, Prevention and/or Treatment of Liver Diseases

In a preferred embodiment of the invention the above hydrophobic modified preS-derived peptides, in particular their conjugates with compounds, are provided for the diagnosis, prevention and/or treatment of a liver disease or disorder.

Depending on the liver disease or disorder which shall be diagnosed, prevented and/or treated the respective compound is selected and selectively, specifically delivered to the liver.

A "liver disease" or a "liver disorder" according to the present invention refers to any disease or disorder that has an effect on or involves the organ liver, liver tissue or hepatocytes.

Examples of liver diseases are:
Hepatitis: inflammation of the liver, caused mainly by various viruses but also by certain poisons, autoimmunity or hereditary conditions;
Cirrhosis: the formation of fibrous tissue in the liver, replacing dead liver cells. The death of the liver cells can for example be caused by viral hepatitis, alcoholism or contact with other liver-toxic chemicals;

Haemochromatosis: a hereditary disease causing the accumulation of iron in the body, eventually leading to liver damage;

Cancer of the liver: primary hepatocellular carcinoma (HCC) or cholangiocarcinoma and metastatic cancers, usually from other parts of the gastrointestinal tract;

Wilson's disease: a hereditary disease which causes the body to retain copper;

Primary sclerosing cholangitis: an inflammatory disease of the bile duct, autoimmune in nature;

Primary biliary cirrhosis: autoimmune disease of small bile ducts;

Budd-Chiari syndrome: obstruction of the hepatic vein;

Gilbert's syndrome: a genetic disorder of bilirubin metabolism, found in about 5% of the population;

Glycogen storage disease type II: the build-up of glycogen causes progressive muscle weakness (myopathy) throughout the body and affects various body tissues, particularly in the heart, skeletal muscles, liver and nervous system;

pediatric liver disease, such as biliary atresia, alpha-1-antitrypsin deficiency, alagille syndrome, and progressive familial intrahepatic cholestasis;

metabolic diseases.

Furthermore, also liver diseases of animals, such as pets or livestock, are included, in particular diseases that can be transmitted to humans, such as toxoplasmosis.

The liver disease or disorder to be diagnosed, prevented and/or treated is preferably selected from hepatitis, cirrhosis, haemochromatosis, preferably hepatitis caused by hepatitis A, B, C, D, E, F, G and H virus.

The liver disease or disorder to be diagnosed, prevented and/or treated can also be concomitant hepatitis caused by viruses, such as viruses of the family Herpesviridae, e.g. herpes virus, cytomegalie virus (CMV) but also varicella zoster virus (VZV), Epstein Barr virus (EBV), coxsackie viruses, yellow fever virus, Dengue virus.

The liver disease or disorder to be diagnosed, prevented and/or treated can also be a disease which involves a liver stadium of a virus or a non-viral pathogen, such as in many tropical diseases. Since the liver stadium of some pathogens is an early stadium, the respective infection can be selectively, specifically treated in such an early stadium.

Such viruses are hepatitis A, B, C, D, E, F, G and H virus, herpes viruses.

Such non-viral pathogens are bacteria, parasites and/or worms.

Parasites are for example protozoan parasites of the genus *Plasmodium* that cause malaria, such as *Plasmodium falciparum*, *Plasmodium vivax*, and related species (e.g. *Plasmodium ovale*, *Plasmodium malariae*, *Plasmodium knowlesi*).

Such worms are for example flatworms of the genus *Schistosoma* that cause schistosomiasis or bilharziosis, such as *Schistosoma mansoni*, *Schistosoma intercalatum*, *Schistosoma haematobium*, *Schistosoma japonicum* and *Schistosoma mekongi*.

Such parasites are also for example *Leishmania* trypanosome protozoa of the genus *Phlebotomus* and *Lutzomyia* which are responsible for the disease leishmaniasis.

Therefore, malaria, schistosomiasis (bilharziosis), and/or leishmaniasis can be diagnosed, prevented and/or treated by the means of this invention.

Therefore, certain tropical diseases can be diagnosed, prevented and/or treated by the means of this invention.

The liver disease or disorder to be diagnosed, prevented and/or treated are preferably liver tumors, preferably hepatocellular carcinoma (HCC).

The liver disease or disorder to be diagnosed, prevented and/or treated can also be a metabolic disease, such as diabetes, hyperlipidemia, metabolic syndrome and obesity, chronic hyperglycemia, metabolic syndrome, non-alcoholic steatohepatitis (NASH) (see also (9)).

In a preferred embodiment of the invention the above hydrophobic modified preS-derived peptides, in particular their conjugates with compounds, are provided for the regulation of liver function.

Preferred is their use for hepatocyte-mediated antigen presentation and activation of liver-directed immunological responses. In this case, the compound to be delivered to the liver is preferably an immunogenic epitope.

In a preferred embodiment of the invention the above described hydrophobic modified preS-derived peptides, in particular their conjugates with compounds, are also suitable for the prevention of hepatitis B and/or D infection. This is possible due to the property of the above described hydrophobic modified preS-derived peptides to target not only the liver (liver tropism) but furthermore act as viral entry inhibitors of HBV and/or HDV, which can be seen e.g. in FIG. 9. Thus, the above described hydrophobic modified preS-derived peptides are suitable HBV and/or HDV vaccines. (See also corresponding PCT patent application of the inventors with the title: "Hydrophobic modified preS-derived peptides of hepatitis B virus (HBV) and their use as HBV and HDV entry inhibitors", which was filed at the same day.)

Thus, the above described acylated preS-derived peptides, in particular their conjugates with compounds, can be provided for the combined diagnosis, prevention and/or treatment of a liver disease or disorder and the prevention of hepatitis B and/or D infection.

In a preferred embodiment of the invention the above described acylated preS-derived peptides, in particular their conjugates with compounds, can be used for the manufacture of a medicament for the diagnosis, prevention and/or treatment of a liver disease or disorder.

Pharmaceutical Compositions

As outlined above, the present invention provides a pharmaceutical composition comprising at least one hydrophobic modified preS-derived peptide of HBV as defined herein and at least a compound to be specifically delivered to the liver as defined herein and optionally a pharmaceutically acceptable carrier and/or excipient.

The pharmaceutical composition according to the present invention comprises:
- at least one hydrophobic modified preS-derived peptide of HBV as defined herein above;
- at least a compound to be specifically delivered to the liver, preferably to hepatocytes, as defined herein above;

or

- a conjugate as defined herein;

and

- optionally a pharmaceutically acceptable carrier and/or excipient.

The pharmaceutical compositions according to the present invention are very well suited for all the uses and methods described herein.

A "pharmaceutically acceptable carrier or excipient" refers to any vehicle wherein or with which the pharmaceutical or vaccine compositions according to the invention may be formulated. It includes a saline solution such as phosphate buffer saline. In general, a diluent or carrier is selected on the basis of the mode and route of administration, and standard pharmaceutical practice.

Treatment Method

Furthermore, and as outlined above, the present invention provides methods for the diagnosis, prevention and/or treatment of a liver disease or disorder by utilizing the hydrophobic modified preS-derived peptide(s) of HBV or the pharmaceutical composition(s) of the invention.

The present invention also provides a method for the combined diagnosis, prevention and/or treatment of a liver disease or disorder and the prevention of HBV and/or HDV infection by administering to a subject a conjugate as defined herein, which comprises a hydrophobic modified preS-derived peptide of HBV and a compound, or a pharmaceutical composition as defined herein.

The method for the combined diagnosis, prevention and/or treatment of a liver disease or disorder and the prevention of hepatitis B and/or D infection according to the present invention comprises
administering to a subject in a therapeutically effective amount
(a) a conjugate comprising an hydrophobic modified preS-derived peptide as defined herein above and at least a compound as defined herein above, wherein the conjugate is as defined herein above; or
(b) a pharmaceutical composition as defined herein above.

Route of Administration

Preferably, the route of administration of the conjugates or pharmaceutical compositions of the present invention, in particular in the method of treatment, is selected from subcutaneous, intravenous, oral, nasal, intramuscular, transdermal, inhalative, by suppository.

A preferred embodiment for nasal administration or application is a nasal spray.

Therapeutically Effective Amount

A "therapeutically effective amount" of a conjugate or a pharmaceutical composition of this invention refers to the amount that is sufficient to diagnose, prevent and/or treat the respective liver disease or disorder and/or to prevent hepatitis B and/or D infection.

A preferred therapeutically effective amount is in the range of 10 μg to 1 mg per kg body weight.

For the use of an hydrophobic modified preS-derived peptide of the invention as a vaccine the preferred therapeutically effective amount is in the range of 10 μg to 1 mg per kg body weight.

In case of an $IC_{50}$ value of the hydrophobic modified preS-derived peptide used of about 10 nM, a preferred therapeutically effective amount is about 100 μg per kg body weight or in the range of 1 to 5 mg per patient.

The preferred therapeutically effective amount depends on the respective compound that is to be delivered and its respective therapeutically effective amount.

The skilled artisan will be able to determine suitable therapeutically effective amounts.

Gene Therapy Application

The present invention also provides the preS-derived peptides, i.e. nucleic acids encoding them, in gene therapy approaches.

A viral vector is provided that comprises a nucleic acid encoding a preS-derived peptide P as defined herein for the gene therapy of a liver disease or disorder. The nucleic acid encodes the amino acid sequence of the preS-derived peptide P, which is necessary and sufficient to accomplish liver targeting.

Preferably, the viral vector is replication defective, preferably an adeno-associated viral vector.

In an embodiment the viral vector further comprises a heterologous sequence to be expressed in the liver.

The viral vector is preferably a gene therapeutically suitable vector, which are known to the skilled person.

Identification of the HBV Receptor

The invention further relates to a method for in vitro and/or in vivo identification of a hepatocyte receptor involved in the attachment and/or penetration of HBV and/or quantitation of the expression of said receptor that comprises using a hydrophobic modified preS-derived peptide as described above.

Said hepatocyte receptor can be identified in mammals or respective animal models, preferably mouse or human.

In particular, said method comprises the steps comprising:
contacting a liver biopsy or a hepatocyte with a hydrophobic modified preS-derived peptide of the invention under conditions and for a period of time sufficient to allow specific binding of said peptide to a receptor expressed at the surface of a hepatocyte;
detecting binding of said peptide to a receptor; and
identifying said receptor.

The method for the identification of a HBV receptor comprises the use of
(a) a conjugate comprising a hydrophobic modified preS-derived peptide as defined herein and at least a compound as defined herein, wherein the conjugate is as defined herein; or
(b) a pharmaceutical composition as defined herein.

This can be achieved according to classical procedures well-known by the skilled in the art. For instance, this could involve radioactive, enzyme or fluorescent labelling of the hydrophobic modified preS-derived peptides of the invention, and subsequent detection with an appropriate method. A number of fluorescent materials are known and can be utilized as labels. These include, for example, fluorescein, rhodamine, auramine, Texas Red. Enzyme labels comprise conjugation of an enzyme to a molecule of interest, e.g. a polypeptide, and can be detected by any of colorimetric, spectrophotometric, or fluorospectrophotometric techniques.

The human Hepatitis B Virus (HBV) is the most important etiological factor of hepatocellular carcinoma. Hallmarks of HBV infection are a remarkable in vivo efficacy and a pronounced liver tropism. The latter is probably the result of a specific interaction of one of the three HBV surface proteins with liver associated receptors or liver-targeting factors in the circulation system.

Based on recent insights into molecular details of the HBV entry pathway and the identification of HBV-surface protein domains which are responsible for hepatocyte binding and liver tropism, the present invention led to the development of a new class of peptide-drug conjugates to target liver diseases, such as HCC, and optionally to interfere with HBV and HDV infection.

The inventors identified HBV-preS1-surface protein-derived lipopeptides that efficiently block HBV entry in vitro and in vivo. Biodistribution studies of the present invention on these inhibitory peptides revealed that they selectively accumulate in the liver were they bind to and presumably enter into hepatocytes. This hepatotropism requires N-terminal acylation of the peptide and depends on a certain HBV preS-sequence motif within the N-terminal 47 preS1 amino acids, i.e. within the amino acid residues 2 to 21 or amino acid residues 2 to 20 (or preferably the minimal sequence of residues 9 to 15). The inventors' observation that this peptide sequence additionally bears a membrane translocation signal which facilitates the transport of even complete fusion proteins across plasma membranes (unpublished results) opens the possibility of specifically delivering any kind of drug to the plasma membrane of hepatocytes or selectively even into this cell.

The inventors have shown that HBV preS1-derived lipopeptides are capable to completely prevent HBV infection in a transplanted uPA-RAG-1 mouse model at very low doses. Pharmakokinetic studies on these HBVpreS-derived entry inhibitors indicated a remarkable hepatotropism combined with an extraordinary high serum stability ($t_{1/2}$ ca. 60 h) and a long half life time in the target organ ($t_{1/2}$ ca. 24 h). Both N-terminal acylation as well as the integrity of the certain amino acid sequence of the peptides are mandatory (i.e. within the amino acid residues 2 to 21 (or preferably the minimal sequence of residues 9 to 15)). The peptides can be used as versatile vectors for liver specific drug targeting to conquer infections of hepatocytes or to treat hepatocellular carcinoma.

The inventors have furthermore proven the principle that WMHBV infection can be efficiently blocked through subcutaneous application of HBV envelope protein-derived peptides in vivo. This opens new perspectives for the prevention of acute HBV-infection and therapeutic options for chronic hepatitis B. Since the uPA/RAG-2/Pfp mice used lack B cells, T cells, and NK cells, a direct inhibitory effect of the peptides on susceptible hepatocytes is assumed. This is supported by the efficient accumulation of acylated preS-derived peptides in the liver, followed by a slow clearance possibly via the biliary route. Both properties permit subcutaneous application at very low doses and low frequencies. Given that 5 injections of 0.2 mg/kg HBV/preS2-48$^{myr}$ within 5 days resulted in the prevention of the establishment of WMHBV infection, continuous administration of the about 30-fold more active peptide HBV/preS2-48$^{stearoyl}$ might be effective at doses below 7 µg/kg≈13 nmol/kg when given daily or every 2 days. Taking into account that the efficient pharmacological dose per body weight obtained in mice has to be corrected for humans (8) by a factor of about 10, the efficient dose per person is expected to be lower than 100 µg/day.

The inventors have also shown that

- the HBV preS1-derived lipopeptides of the invention bind to primary human hepatocytes (PHH) and that this binding is myristoyl-dependent and sequence specific (see also FIG. 10),
- Binding of the HBV preS1-derived lipopeptides of the invention is not restricted to HBV-susceptible hepatocytes (see also FIG. 11),
- Binding of the HBV preS1-derived lipopeptides of the invention depends on the differentiation state of the cells and that they only bind to differentiated hypocytes (see FIG. 12),
- the HBV preS1-derived lipopeptides of the invention do not bind to other hepatoma and non-hepatoma cell lines
  - no binding was seen to Hep G2 cells, Hep G2.215 cells, HuH 7 cells and CHO K1 cells (data not shown)

Thus, cellular factors addressed by the peptides depend on the differentiation state. But these are not critical for the restricted host-range of the virus.

TABLE 1

Preferred hydrophobic modified preS-derived peptides

| Designation of peptide | | Amino acid sequence |
|---|---|---|
| HBVpreS/(−11)-48(consensus) | consensus | SEQ ID NO. 1 |
| HBVpreS/2-48$^{myr}$(consensus) | | SEQ ID NO. 11 |
| HBVpreS/2-48$^{stearoyl}$(consensus) | | |
| HBVpreS/2-21$^{myr}$(consensus) | | SEQ ID NO. 12 |
| HBVpreS/2-21$^{stearoyl}$(consensus) | | |
| Genotype C peptides | | |
| *HBVpreS/(−11)-48$^{myr}$(C) | natural | SEQ ID NO. 4 |
| *HBVpreS/(−11)-48$^{stearoyl}$(C) | | |
| *HBVpreS/2-48$^{myr}$(C) | | SEQ ID NO. 13 |
| *HBVpreS/2-48$^{stearoyl}$(C) | | |
| HBVpreS/5-48$^{myr}$(C) | truncated N-terminal | SEQ ID NO. 14 |
| HBVpreS/5-48$^{stearoyl}$(C) | | |
| HBVpreS/9-48$^{myr}$(C) | | SEQ ID NO. 15 |
| HBVpreS/9-48$^{stearoyl}$(C) | | |
| HBVpreS/2-21$^{myr}$(C) | truncated N- and/or C-terminal | SEQ ID NO. 16 |
| HBVpreS/2-21$^{stearoyl}$(C) | | |
| HBVpreS/5-21$^{myr}$(C) | | SEQ ID NO. 17 |
| HBVpreS/5-21$^{stearoyl}$(C) | | |
| HBVpreS/9-21$^{myr}$(C) | | SEQ ID NO. 18 |
| HBVpreS/9-21$^{stearoyl}$(C) | | |
| HBVpreS/2-15$^{myr}$(C) | | SEQ ID NO. 19 |
| HBVpreS/2-15$^{stearoyl}$(C) | | |
| HBVpreS/5-15$^{myr}$(C) | | SEQ ID NO. 20 |
| HBVpreS/5-15$^{stearoyl}$(C) | | |
| HBVpreS/9-15$^{myr}$(C)** | | SEQ ID NO. 21 |
| HBVpreS/9-15$^{stearoyl}$(C)** | | |
| HBVpreS/(−2)-20$^{palm}$(C) | | SEQ ID NO. 22 |
| Genotype D peptides | | |
| HBVpreS/1-48$^{myr}$(D) | natural | SEQ ID NO. 5 |
| HBVpreS/2-48$^{myr}$(D) | | SEQ ID NO. 23 |
| HBVpreS/2-48$^{stearoyl}$(D) | | |
| HBVpreS/5-48$^{myr}$(D) | truncated N-terminal | SEQ ID NO. 24 |
| HBVpreS/5-48$^{stearoyl}$(D) | | |
| HBVpreS/9-48$^{myr}$(D) | | SEQ ID NO. 25 |
| HBVpreS/9-48$^{stearoyl}$(D) | | |
| HBVpreS/2-21$^{myr}$(D) | N- and/or C-terminal | SEQ ID NO. 26 |
| HBVpreS/2-21$^{stearoyl}$(D) | | |
| HBVpreS/5-21$^{myr}$(D) | | SEQ ID NO. 27 |
| HBVpreS/5-21$^{stearoyl}$(D) | | |
| HBVpreS/9-21$^{myr}$(D) | | SEQ ID NO. 28 |
| HBVpreS/9-21$^{stearoyl}$(D) | | |
| HBVpreS/2-20$^{myr}$(D) | | SEQ ID NO. 38 |
| HBVpreS/2-20$^{stearoyl}$(D) | | |
| HBVpreS/2-15$^{myr}$(D) | | SEQ ID NO. 29 |
| HBVpreS/2-15$^{stearoyl}$(D) | | |
| HBVpreS/5-15$^{myr}$(D) | | SEQ ID NO. 30 |
| HBVpreS/5-15$^{stearoyl}$(D) | | |
| HBVpreS/9-15$^{myr}$(D)** | | SEQ ID NO. 21 |
| HBVpreS/9-15$^{stearoyl}$(D)** | | |

$^{myr}$refers to myristoylation of the N-terminus;
$^{palm}$refers to palmitoylation of the N-terminus;
$^{stearoyl}$refers to stearoylation of the N-terminus;
(C)refers to genotype C (with Q46K, as in SEQ ID NO. 4);
(D)refers to genotype D;
**minimal sequence.

TABLE 2

Preferred hydrophobic modified preS-derived peptides with changes in the immunogenic epitopes

| Designation of peptide | Amino acid sequence |
|---|---|
| HBVpreS/2-48$^{myr}$-Ala$^{21,23,29,30}$(C) | SEQ ID NO. 31 |
| HBVpreS/2-48$^{stearoyl}$-Ala$^{21,23,29,30}$(C) | |
| HBVpreS/(−11)-48$^{myr}$-D20A(C) | SEQ ID NO. 32 |
| HBVpreS/(−11)-48$^{stearoyl}$-D20A(C) | |
| HBVpreS/2-48$^{myr}$-D20A(C) | SEQ ID NO. 33 |
| HBVpreS/2-48$^{stearoyl}$-D20A(C) | |
| HBVpreS/(−11)-48$^{myr}$-SNN(27-29)ANA(C) | SEQ ID NO. 34 |
| HBVpreS/(−11)-48$^{stearoyl}$-SNN(27-29)ANA(C) | |

TABLE 2-continued

Preferred hydrophobic modified preS-derived peptides
with changes in the immunogenic epitopes

| Designation of peptide | Amino acid sequence |
|---|---|
| HBVpreS/2-48$^{myr}$-SNN(27-29)ANA(C) HBVpreS/2-48$^{stearoyl}$-SNN(27-29)ANA(C) | SEQ ID NO. 35 |
| HBVpreS/(−11)-48$^{myr}$-D20A + SNN(27-29)ANA(C) HBVpreS/(−11)-48$^{stearoyl}$-D20A + SNN(27-29)ANA(C) | SEQ ID NO. 36 |
| HBVpreS/2-48$^{myr}$-D20A + SNN(27-29)ANA(C) HBVpreS/2-48$^{stearoyl}$-D20A + SNN(27-29)ANA(C) | SEQ ID NO. 37 |

$^{myr}$refers to myristoylation of the N-terminus;
$^{stearoyl}$refers to stearoylation of the N-terminus;
(C)refers to genotype C (with Q46K, as in SEQ ID NO. 4);

The following examples and drawings illustrate the present invention without, however, limiting the same thereto.

BRIEF DESCRIPTION OF THE DRAWINGS

FIG. 3. Biodistribution and liver stability of HBVpreS-derived lipopeptides after subcutaneous application.
(A) Liver-specific accumulation of myristoylated ($C_{14}$) versus stearoylated ($C_{18}$) HBV preS/2-48 (D) peptides after subcutaneous injection in male NMRI mice in comparison to the control Fuzeon® (T-20). Per animal approximately 2.25 µg of the $^{131}$I-labelled peptides were subcutaneously injected. At the indicated time points animals were sacrificed and the liver specific peptide accumulation (% ID/g) was determined.
(B) Reversed phase HPLC of pure $^{131}$I-labelled HBVpreS/2-48$^{myr}$(D) (brown curve) in comparison to liver extracts (orange curve) obtained 24 h post subcutaneous injection into uPA+/−/RAG-2-/−/Pfp-/− mice of the same peptide. Note that 50% of detectable activity is eluting at fraction 13. Since the hydrophobic myristoyl residue is located at the N-terminus and the iodinated Tyr-residue at the C-terminus fraction 13 represents the unaltered full-length peptide.

FIG. 7. The liver tropism is sequence specific and requires N-terminal hydrophobic modification.
A and B. Biodistribution of a preS peptide, wherein the N-terminus is not hydrophobic modified, compared to a randomized ("scrambled") sequence. Note that both HBVpreS/1-48 Tyr as well as its randomized form are located to the kidney.
A: Biodistribution of HBVpreS/1-48 Tyr(D) in mice.
B: Biodistribution of HBVpreS/scrambled 1-48 Tyr(D) in mice.
C and D. Biodistribution of a hydrophobic modified preS peptide compared to a randomized ("scrambled") sequence. Only HBVpreS/2-48 Tyr$^{stearoyl}$(D) is transported to the liver, wherein its randomized form is evenly distributed.
C: Biodistribution of HBVpreS/2-48 Tyr$^{stearoyl}$(D) in mice.
D: Biodistribution of HBVpreS/2-48 Tyr (scrambled)$^{stearoyl}$(D) in mice.

B: HBV infection inhibition by HBVpreS/2-48$^{stearoyl}$(D), HBVpreS/2-15$^{stearoyl}$(D), HBVpreS/2-21$^{stearoyl}$(D), HBVpreS/2-26$^{stearoyl}$(D) and HBVpreS/2-33$^{stearoyl}$(D).

HepaRG cells were infected either in absence (0 nM) or in the presence of 1, 5, 25, 100 and 1000 nM of the respective hydrophobic modified HBVpreS-derived peptides of the invention. The infectious inoculum (HBV of genotype D) and the peptides were incubated overnight. After washing, cells were maintained for another 12 days to allow viral gene expression. Cell culture supernatants from day 8-12 were collected and analyzed for secreted HBSAg using a quantitative commercially available ELISA. HBsAg values from the respective uncompleted infection were set to 100% and the degree of infection inhibition is given in % of the uncompleted infection.

Wherein (C) or genotype C refers to HBV genotype C Q46K.

Figure 1:
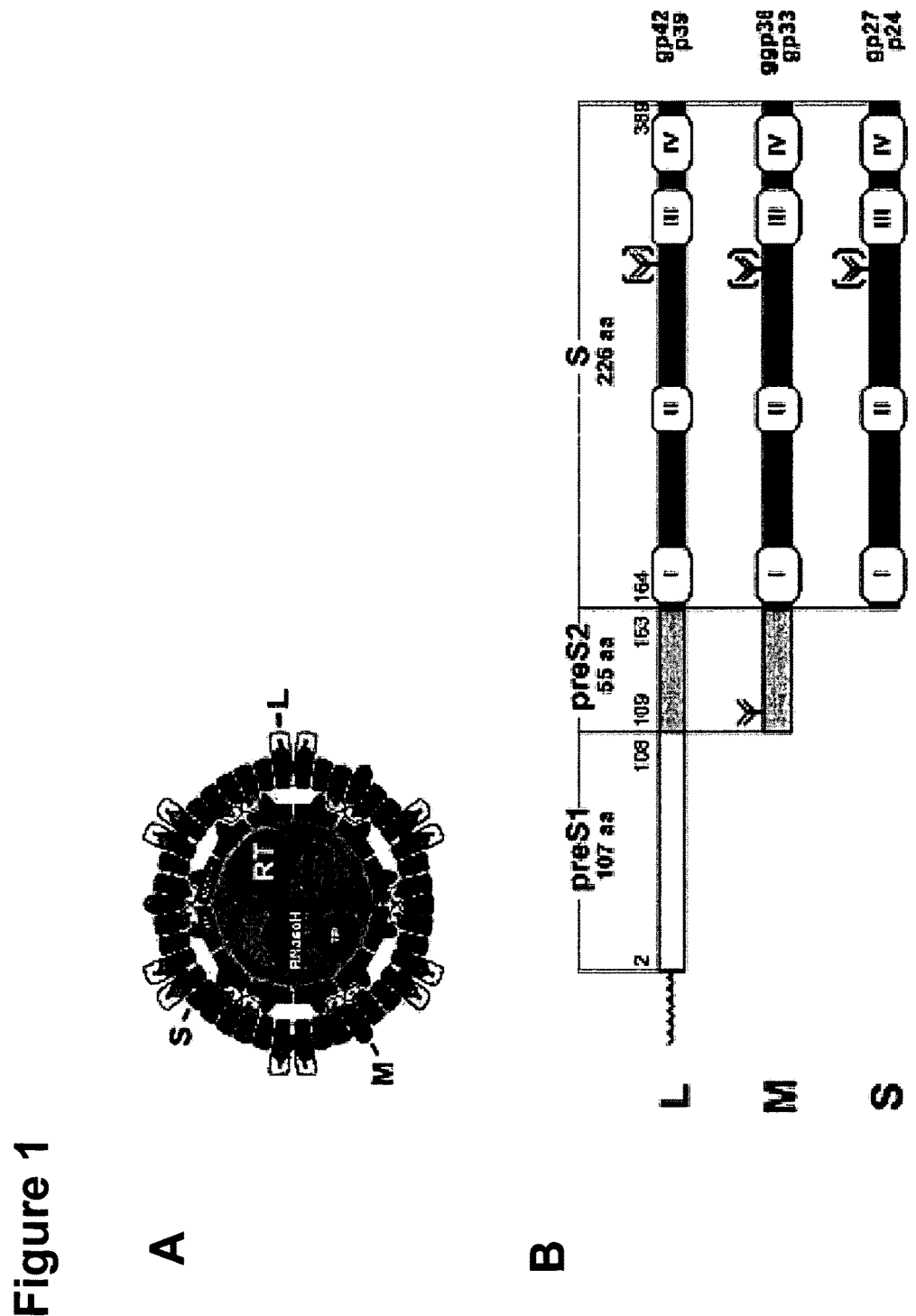
FIG. 1. Schematic representation of the HBV particle and the HBV L-, M- and S-proteins.
(A) The partially double stranded DNA is covalently associated with the viral polymerase complex, consisting of the terminal protein, (TP), the reverse transcriptase (RT) and the RNaseH. The genome is encapsulated by an icosahedral shell, built of 120 core-protein dimers. The 3 HBV surface proteins L-, M- and S- are embedded into an ER-derived lipid bilayer. The L- and M-proteins contain the complete S-domain serving as a membrane anchor.
(B) Domain structure of the 3 HBV surface proteins L, M and S.
The L-protein contains the N-terminally myristoylated 107 amino acid preS1-domain, the 55 amino acid preS2-domain and the S-domain containing the 4 transmembrane segments (I-IV).
Figure 2:
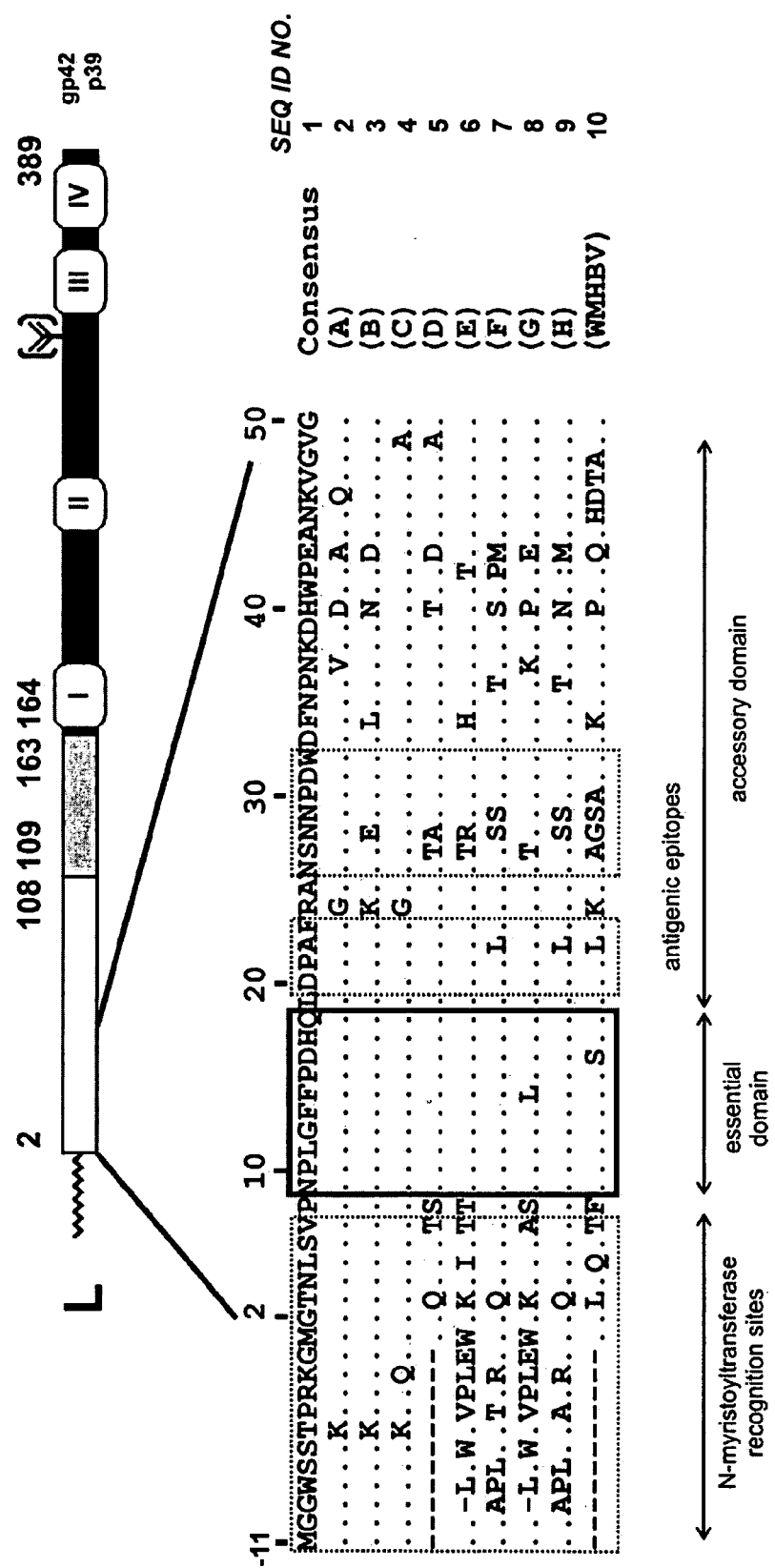
FIG. 2. HBV preS1 consensus sequence.
At the top: the HBV L-protein with its preS1, preS2 and S-domain is depicted. The N-terminus is myristoylated.
The alignment below shows: the consensus sequence (Consensus) and the eight HBV genotypes (A-H) as well as the woolly monkey HBV (WMHBV) preS sequence encompassing amino acids 2-48. Note that the genotypes A, B, C, E, G and H have eleven additional amino acids at their N-termini, genotype F has 10 additional amino acid residues. At the bottom, the known functional subdomains are shown.
Please note that HBV genotype C refers to HBV genotype C Q46K.
Figure 4:
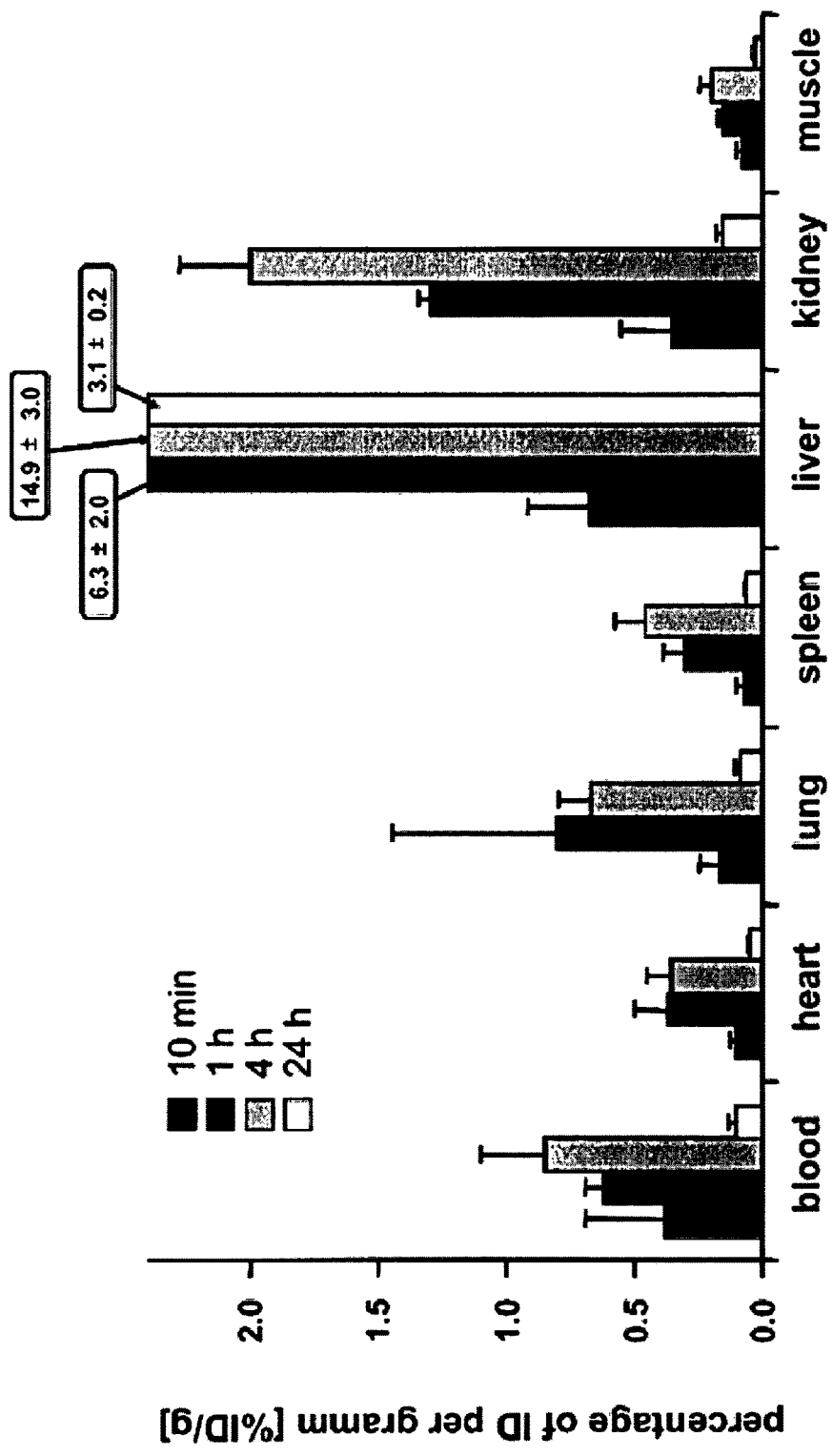
FIG. 4. Biodistribution of HBVpreS/2-48$^{myr}$(D) after subcutaneous application in NMRI mice.
Per time point 2.25 µg of $^{131}$I-labeled HBVpreS/2-48$^{myr}$(D) were subcutaneously injected into NMRI mice (N=3). 10 min, 1 h, 4 h and 24 h post injection animals were sacrificed and the organ-specific (blood, lung, heart, spleen, liver, kidney and muscle) peptide accumulations (% ID/g) were determined. Note that most of the peptide accumulates in the liver and that the Y-axis is jolted for better resolution of the distribution in the other organs.
Figure 5:
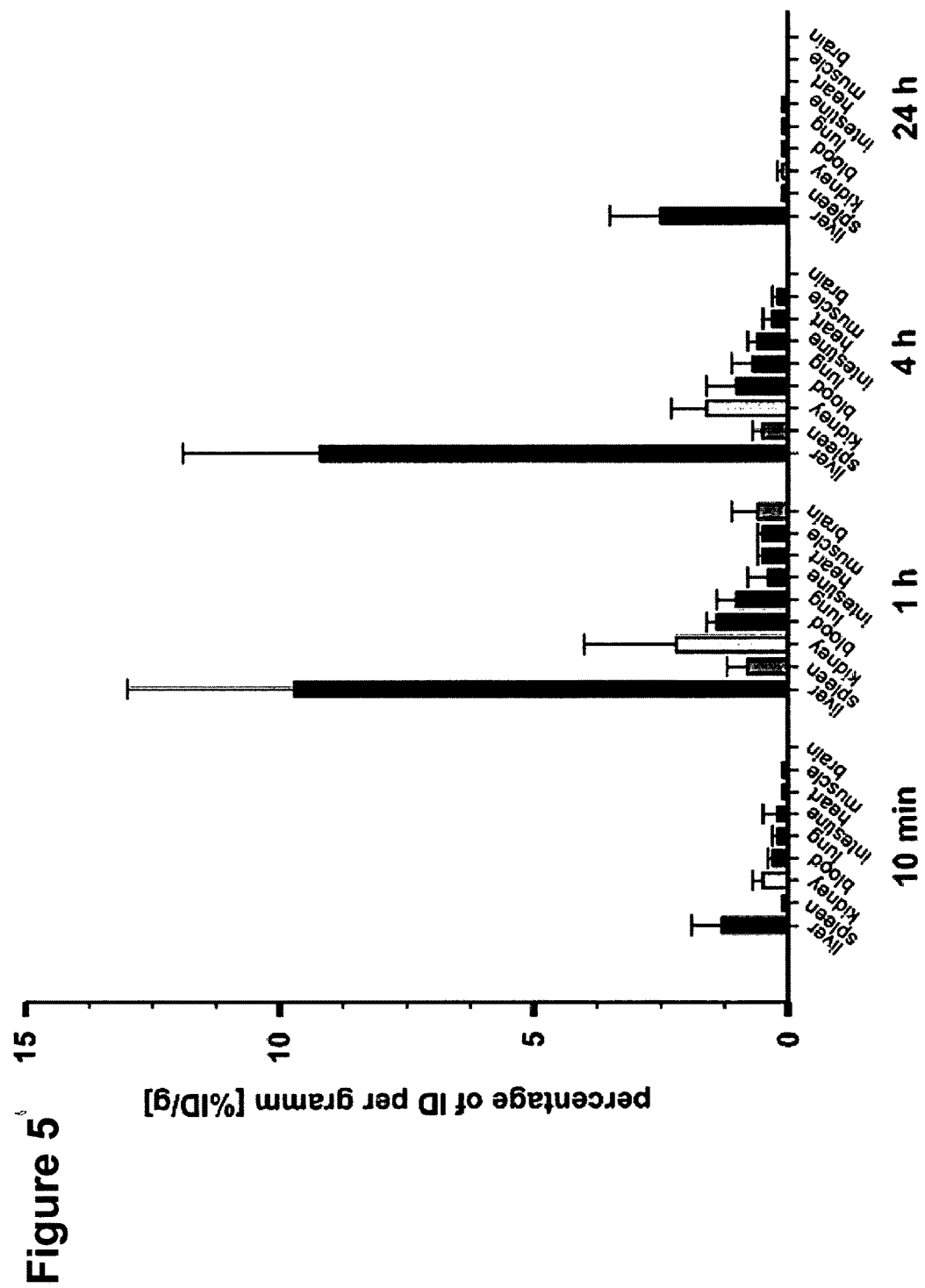
FIG. 5. Biodistribution of HBVpreS/2-48$^{myr}$(D) after subcutaneous application in uPA+/−/RAG-2-/−/Pfp-/− mice.
Per time point 2.25 µg of $^{131}$I-labeled HBVpreS/2-48$^{myr}$(D) were subcutaneously injected (N=3). 10 min, 1 h, 4 h and 24 h post injection animals were sacrificed and the organ-specific (liver, spleen, kidney, blood, lung, intestine, heart, muscle and brain) peptide accumulations (% ID/g) were determined. Note that like in NMRI mice most of the peptide accumulates in the liver.
Figure 6:
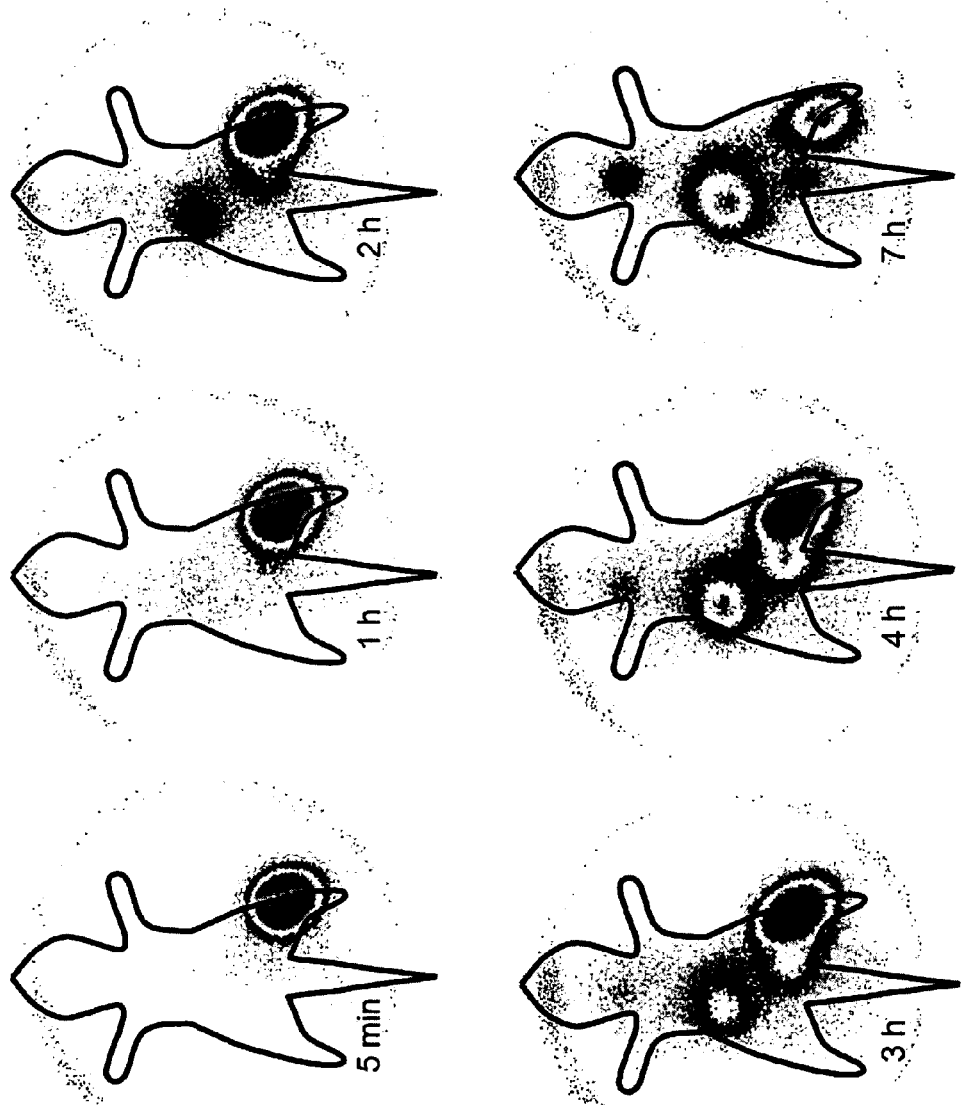
FIG. 6. Scintigram of $^{125}$I-labelled HBVpreS/2-48$^{stearoyl}$(D) after subcutaneous injection in a mouse.
Specific accumulation of $^{125}$I-labelled HBVpreS/2-48$^{stearoyl}$(D) in the liver of mice after subcutaneous injection near the right leg; liver appears on the left side in the middle. Note that the upcoming signal near the head is the thyroid and might represent free iodine after de-iodination of the peptide.
Figure 8:
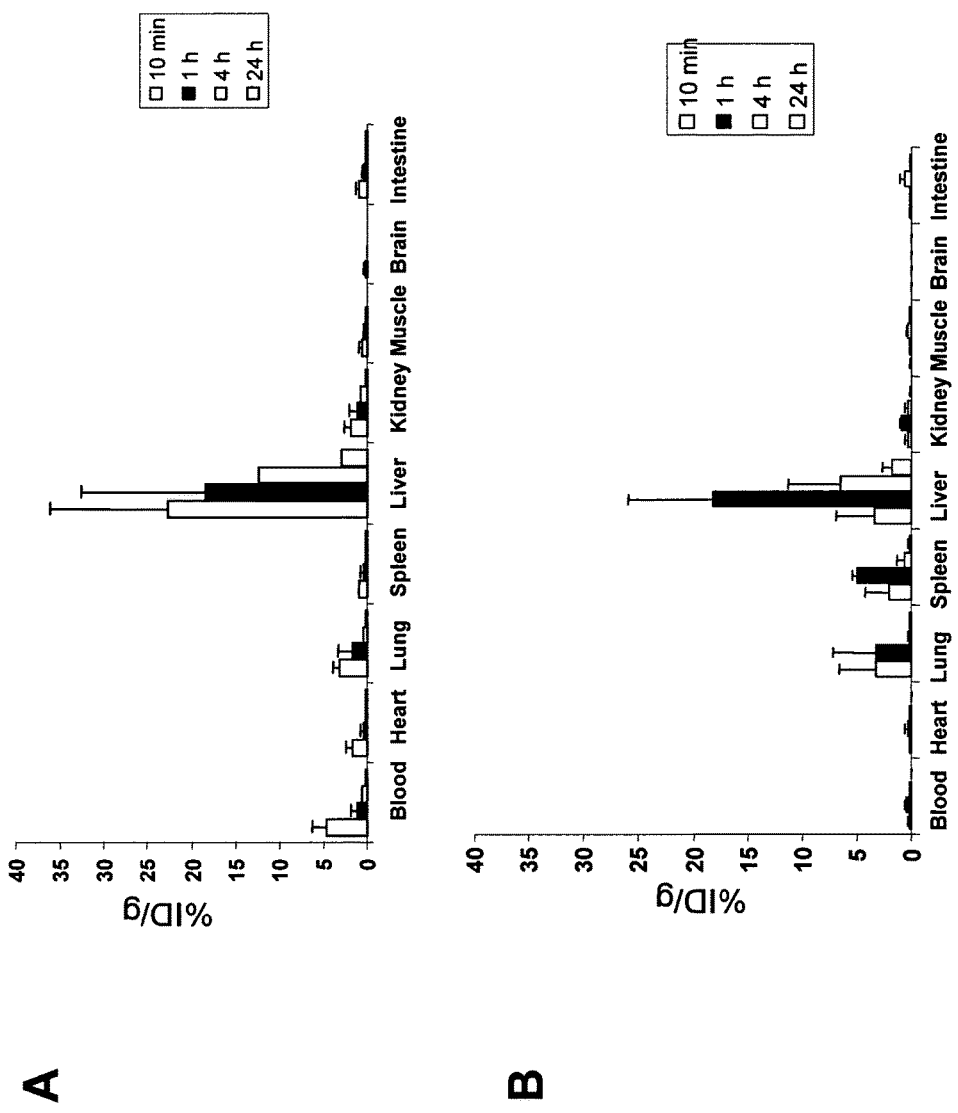
FIG. 8. Biodistribution of variants of hydrophobic modified preS peptides, wherein the variants are N- and/or C-terminal truncated as well as point mutated.
The truncated variants, HBVpreS/5-48 D-Tyr$^{stearoyl}$(D), HBVpreS/2-33-D Tyr$^{stearoyl}$(D) as well as HBVpreS/2-21 D-Tyr$^{stearoyl}$(D), show liver tropism, whereas the variant with a point mutation at position 12 (G12E) does not.
A: Biodistribution of HBVpreS/5-48 D-Tyr$^{stearoyl}$(D) in mice.
B: Biodistribution of HBVpreS/2-33-D Tyr$^{stearoyl}$(D) in mice.
C: Biodistribution of HBVpreS/2-48(G12E) D-Tyr$^{stearoyl}$(D) in mice.
D: Biodistribution of HBVpreS/2-21 D-Tyr$^{stearoyl}$(D) in mice.
Figure 8:
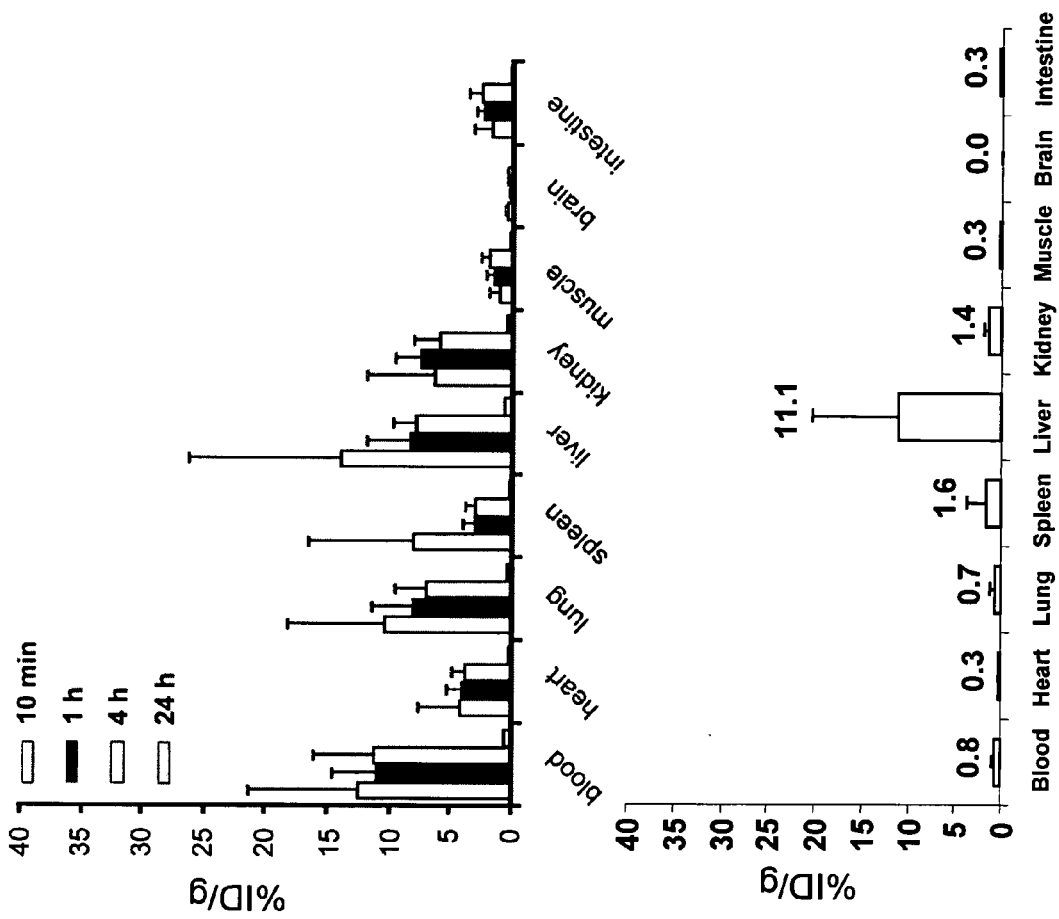
Figure 9:
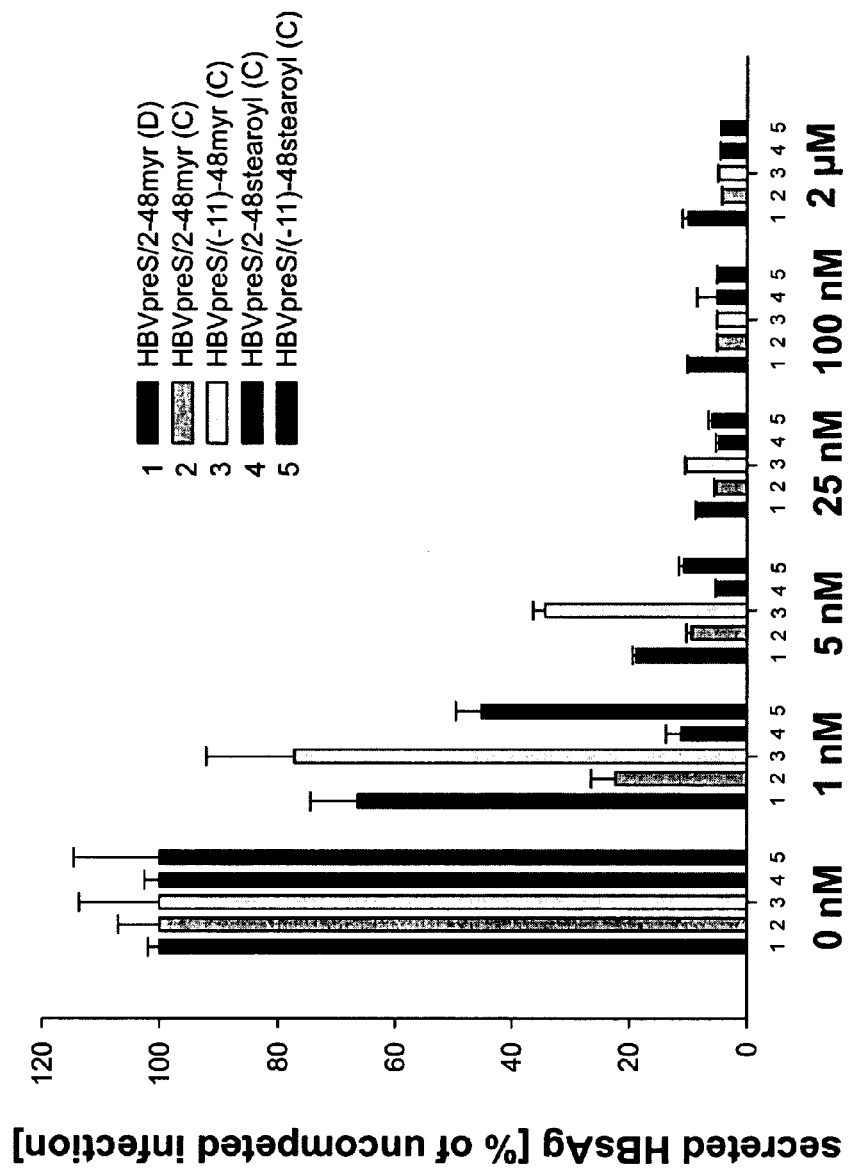
FIG. 9. HBV infection inhibition by hydrophobic modified HBVpreS-derived peptides of the invention.
A: HBV infection inhibition by HBVpreS/2-48$^{myr}$(D), HBVpreS/2-48$^{myr}$(C), HBVpreS/(−11)-48$^{myr}$(C), HBVpreS/2-48$^{stearoyl}$(C) and HBVpreS/(−11)-48$^{stearoyl}$(C).
Figure 9:
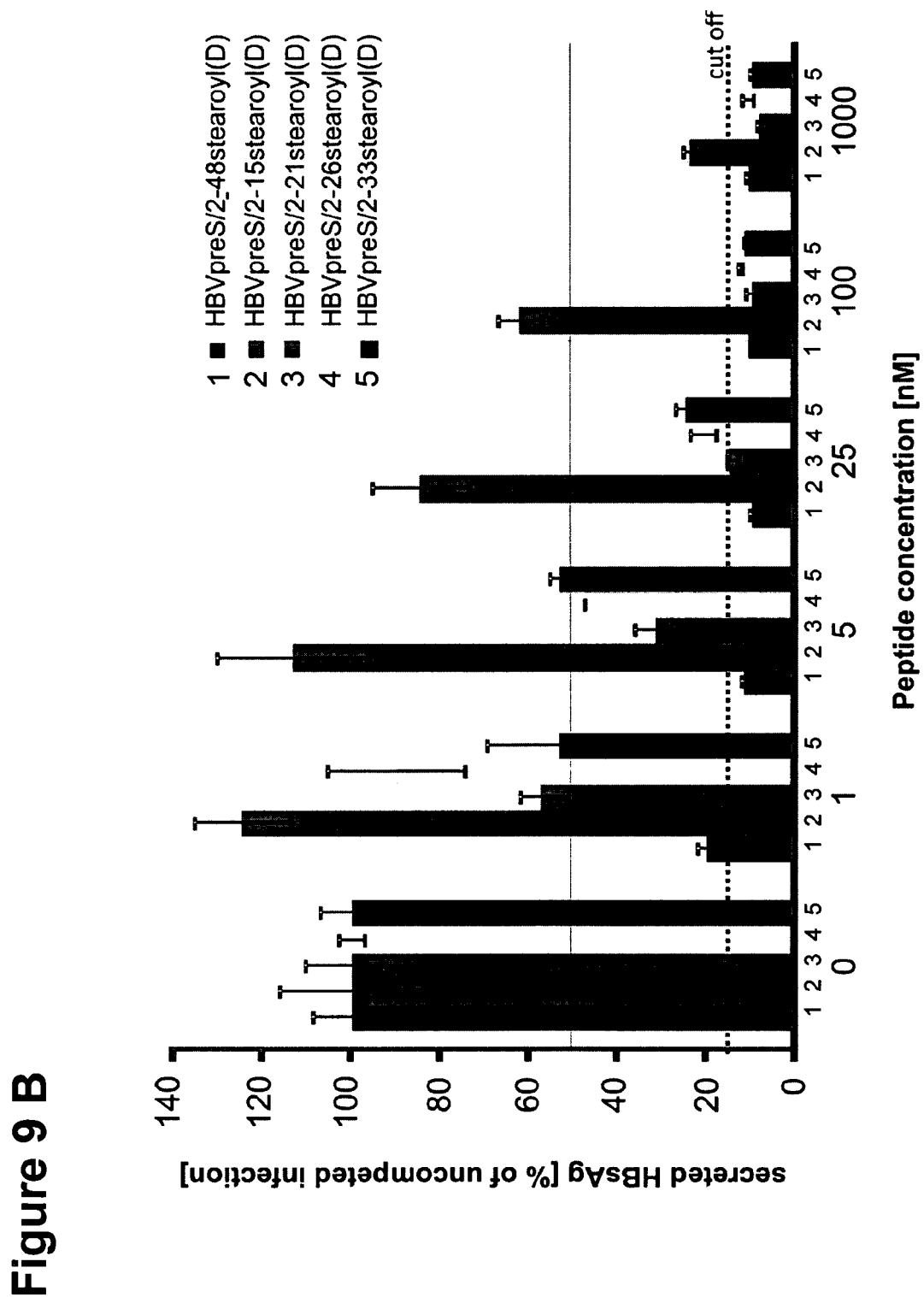
Figure 10:
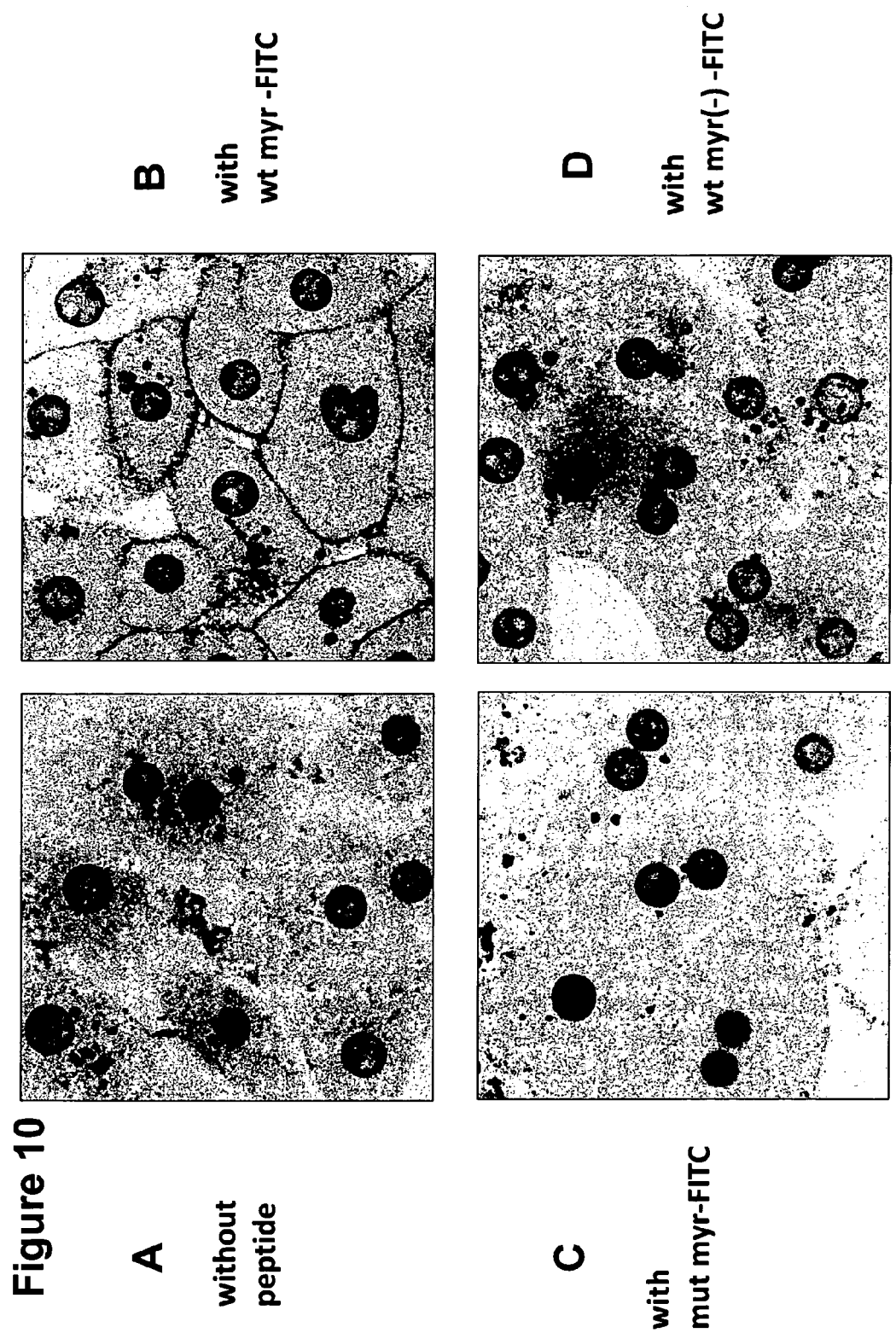

FIG. 10. Binding of the hydrophobic modified HBVpreS-derived peptides of the invention to primary human hepatocytes (PHH) is myristoyl-dependent and sequence specific
Immunofluorescence, showing confocal images Blue: dapi; Green: FITC.
Primary human hepatocytes (PHH) were incubated with or without 400 nM peptide for 4 hours:
A without peptide
B with wt myr-FITC
C with mut myr-FITC
D with wt myr(−)-FITC
Bright (green) dots show autofluorescence of the cells (A, C and D), whereas only in B binding of the peptide to the cells can be seen.
wt myr-FITC refers to HBVpreS/2-48$^{myr}$(C)-FITC with lysine (K) at the C-terminus [SEQ ID NO. 39], labelled with a fluorophor (FITC)
mut myr-FITC HBVpreS/2-48$^{myr}$(C)-FITC with two amino acid substitutions in positions L11 and F13, wherein the amino acids were substituted with the respective D amino acid residues (D-Leu and D-Phe) [SEQ ID NO. 40], labelled with a fluorophor (FITC)
wt myr(−)-FITC refers to HBVpreS/2-48(C)-FITC without myristoylation [SEQ ID NO. 39], labelled with a fluorophor (FITC)
The fluorophor FITC was attached to the sidechain (NFL; group) of the additional Lys.

Figure 11:
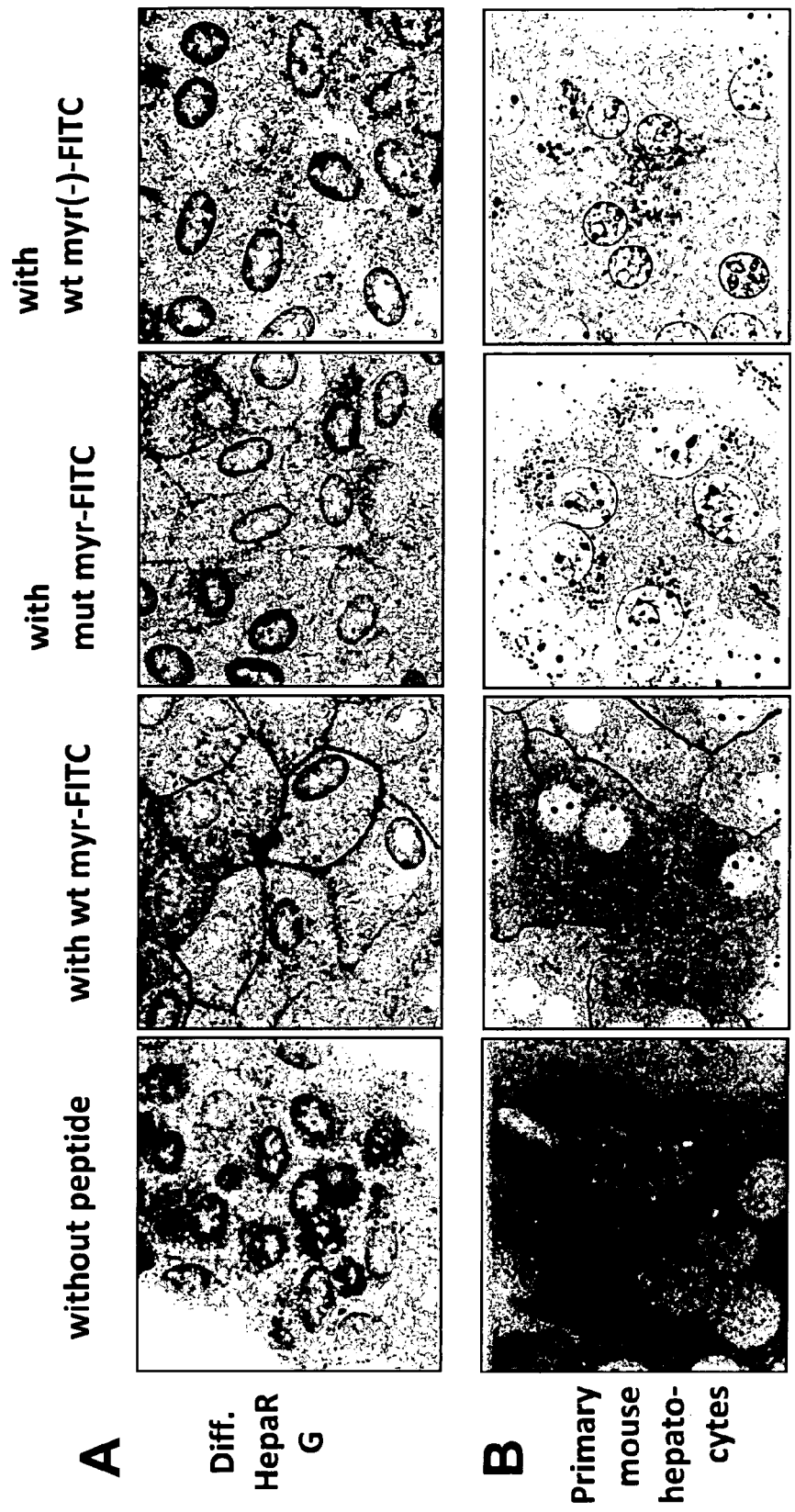

FIG. 11. Binding of the hydrophobic modified HBVpreS-derived peptides of the invention is not restricted to HBV-susceptible hepatocytes.
Immunofluorescence, showing confocal images Blue: dapi; Green: FITC.
Cells were incubated with or without 400 nM peptide for 4 hours at 37° C.:
A (upper panel) Differentiated HepaRG cells
B (lower panel) Primary mouse hepatocytes (PMH)
Only wt myr-FITC binds to the cells. Bright (green) dots show autofluorescence of the cells
wt myr-FITC refers to HBVpreS/2-48$^{myr}$(C)-FITC with lysine (K) at the C-terminus [SEQ ID NO. 39], labelled with a fluorophor (FITC) attached to the sidechain (NH$_2$ group) of the additional Lys
mut myr-FITC HBVpreS/2-48$^{myr}$(C)-FITC with two amino acid substitutions in positions L11 and F13, wherein the amino acids were substituted with the respective D amino acid residues (D-Leu and D-Phe) [SEQ ID NO. 40], labelled with a fluorophor (FITC)
wt myr(−)-FITC refers to HBVpreS/2-48(C)-FITC without myristoylation [SEQ ID NO. 39], labelled with a fluorophor (FITC)
The fluorophor FITC was attached to the sidechain (NH$_2$ group) of the additional Lys.

Figure 12:
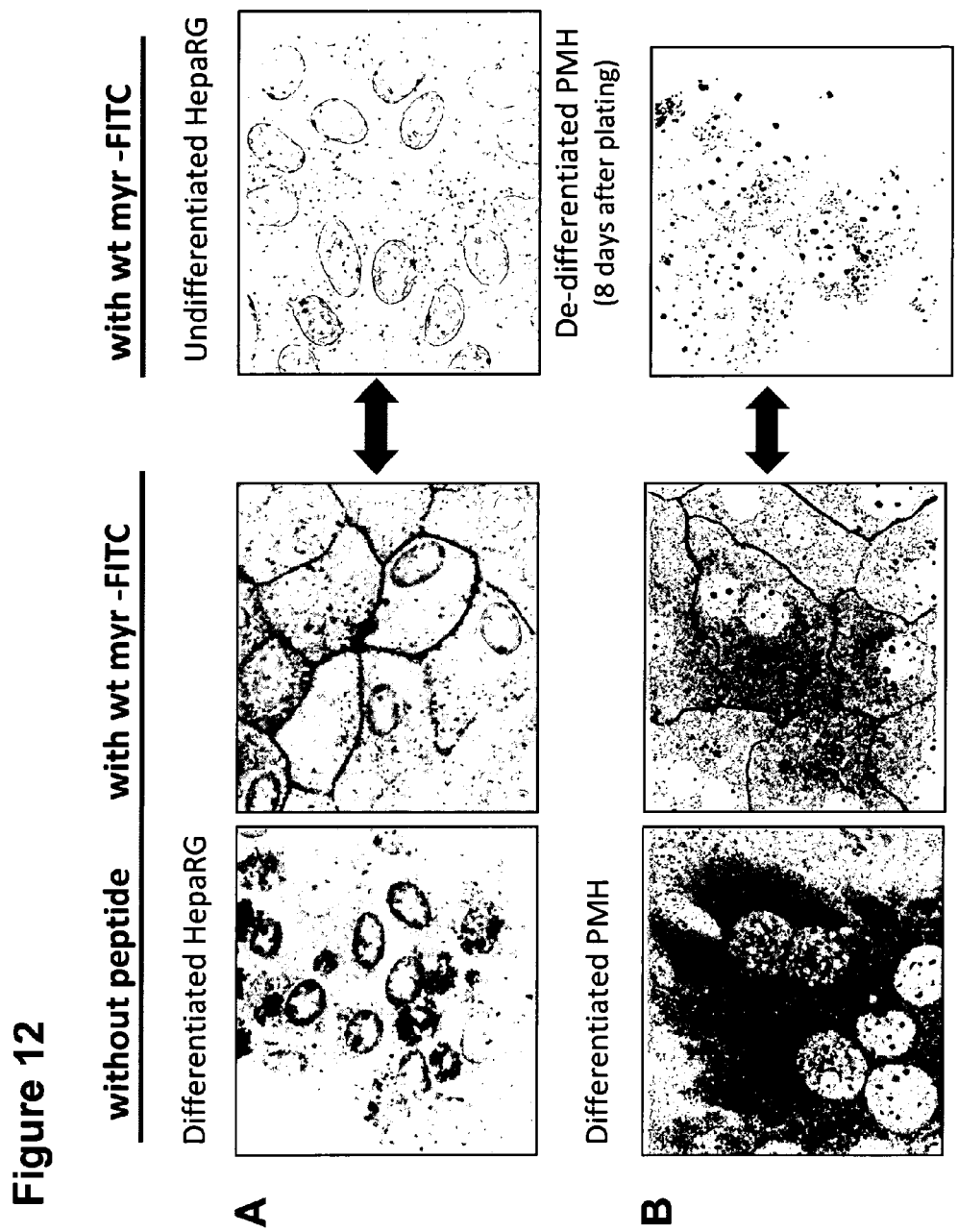

FIG. 12. Binding of the hydrophobic modified HBVpreS-derived peptides of the present invention depends on the differentiation state of the cells. The peptides only bind to differentiated hepatocytes.
Immunofluorescence, showing confocal images Blue: dapi; Green: FITC.
Cells were incubated with or without 400 nM peptide for 4 hours at 37° C.:
A (upper panel) Comparing differentiated and undifferentiated HepaRG cells
B (lower panel) Comparing differentiated and de-differentiated Primary mouse hepatocytes (PMH)
wt myr-FITC binds only to differentiated cells. Bright (green) dots show autofluorescence of the cells
wt myr-FITC refers to HBVpreS/2-48$^{myr}$(C)-FITC with lysine (K) at the C-terminus [SEQ ID NO. 39], labelled with a fluorophor (FITC)
The fluorophor FITC was attached to the sidechain (NH$_2$ group) of the additional Lys.

Figure 13:
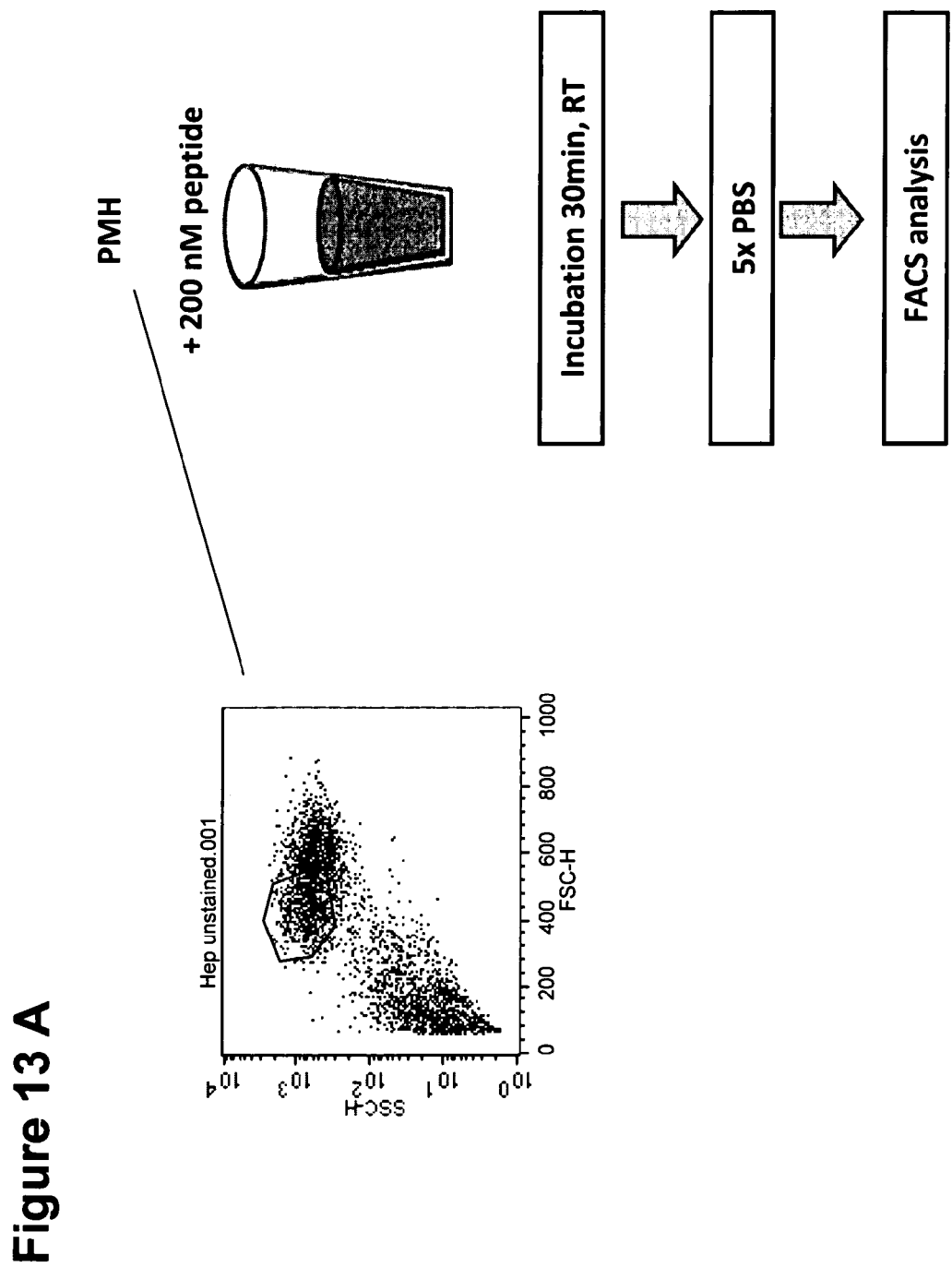
Figure 13:
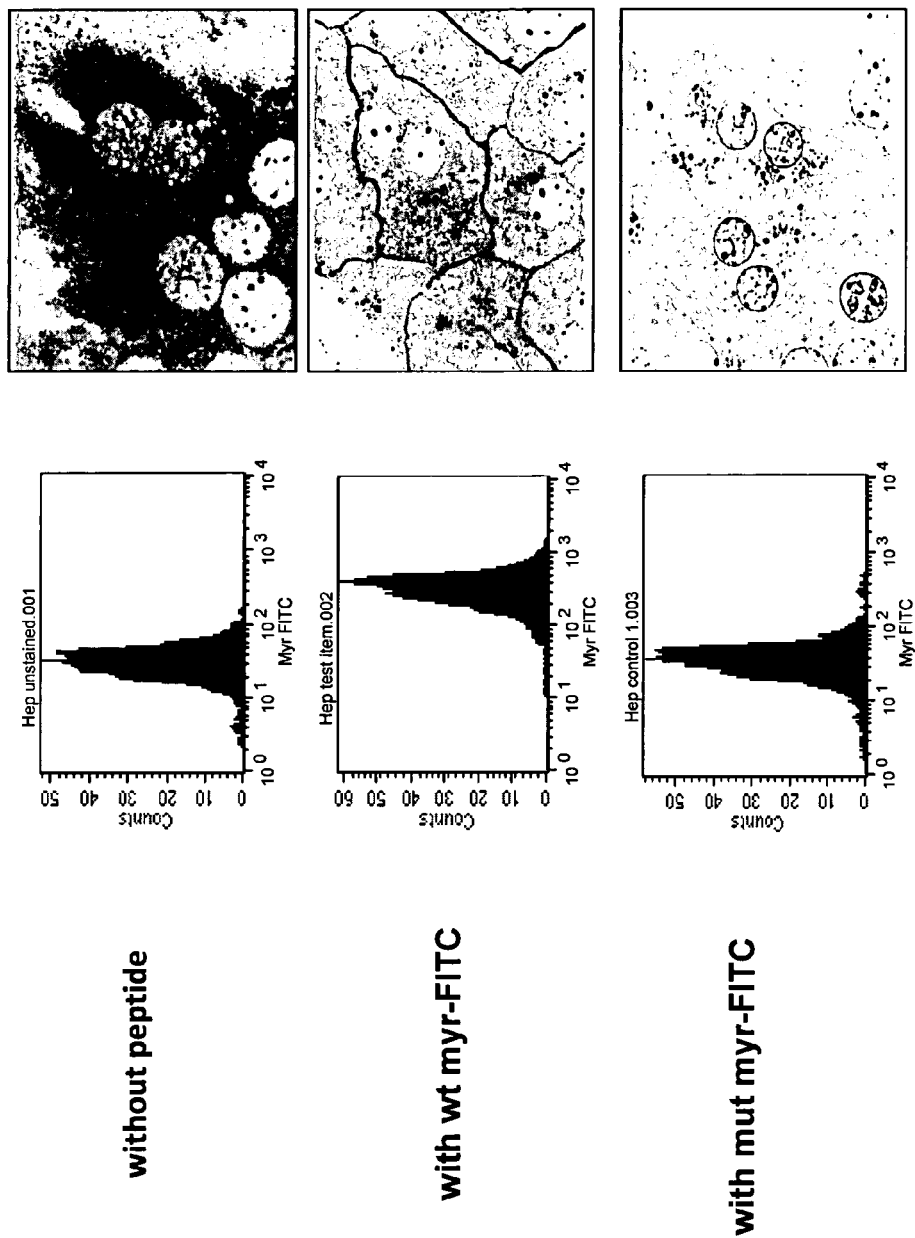

FIG. 13. FACS analysis of the binding of a hydrophobic modified HBVpreS-derived peptide of the present invention to primary mouse hepatocytes (PMH).
A showing the protocol of the FACS analysis
B showing the results of the FACS analysis (in comparison to the immunofluorescence results). Only wt myr-FITC binds to the cells.
wt myr-FITC refers to HBVpreS/2-48$^{myr}$(C)-FITC with lysine (K) at the C-terminus [SEQ ID NO. 41], labelled with a fluorophor (FITC)
mut myr-FITC HBVpreS/2-48$^{myr}$(C)-FITC with two amino acid substitutions in positions L11 and F13, wherein the amino acids were substituted with the respective D amino acid residues (D-Leu and D-Phe) [SEQ ID NO. 42], labelled with a fluorophor (FITC)
The fluorophor FITC was attached to the sidechain (NH$_2$ group) of the additional Lys.

Figure 14:
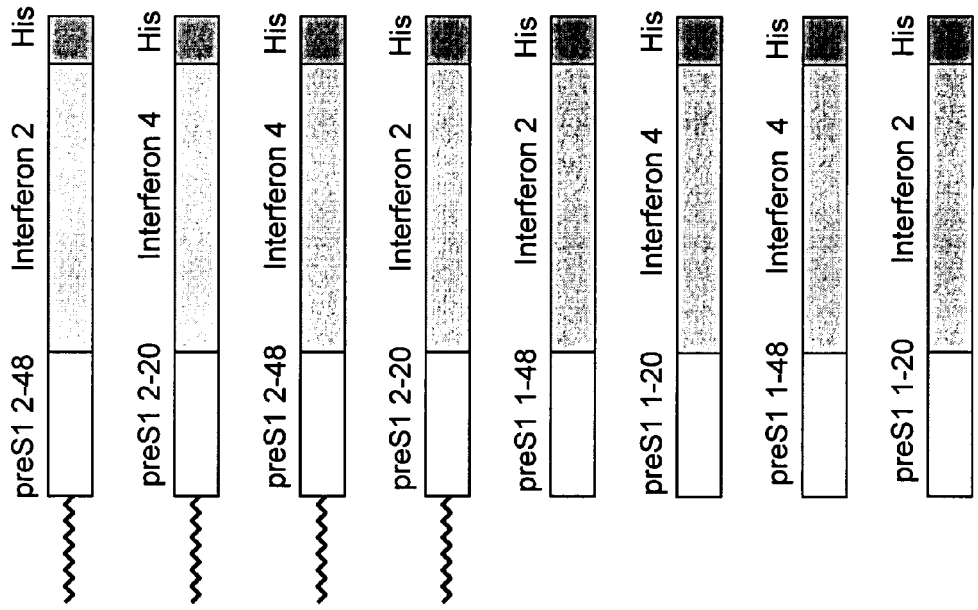

FIG. 14. Fusion constructs of HBVpreS-derived peptides with mouse interferon alpha.

Figure 15:
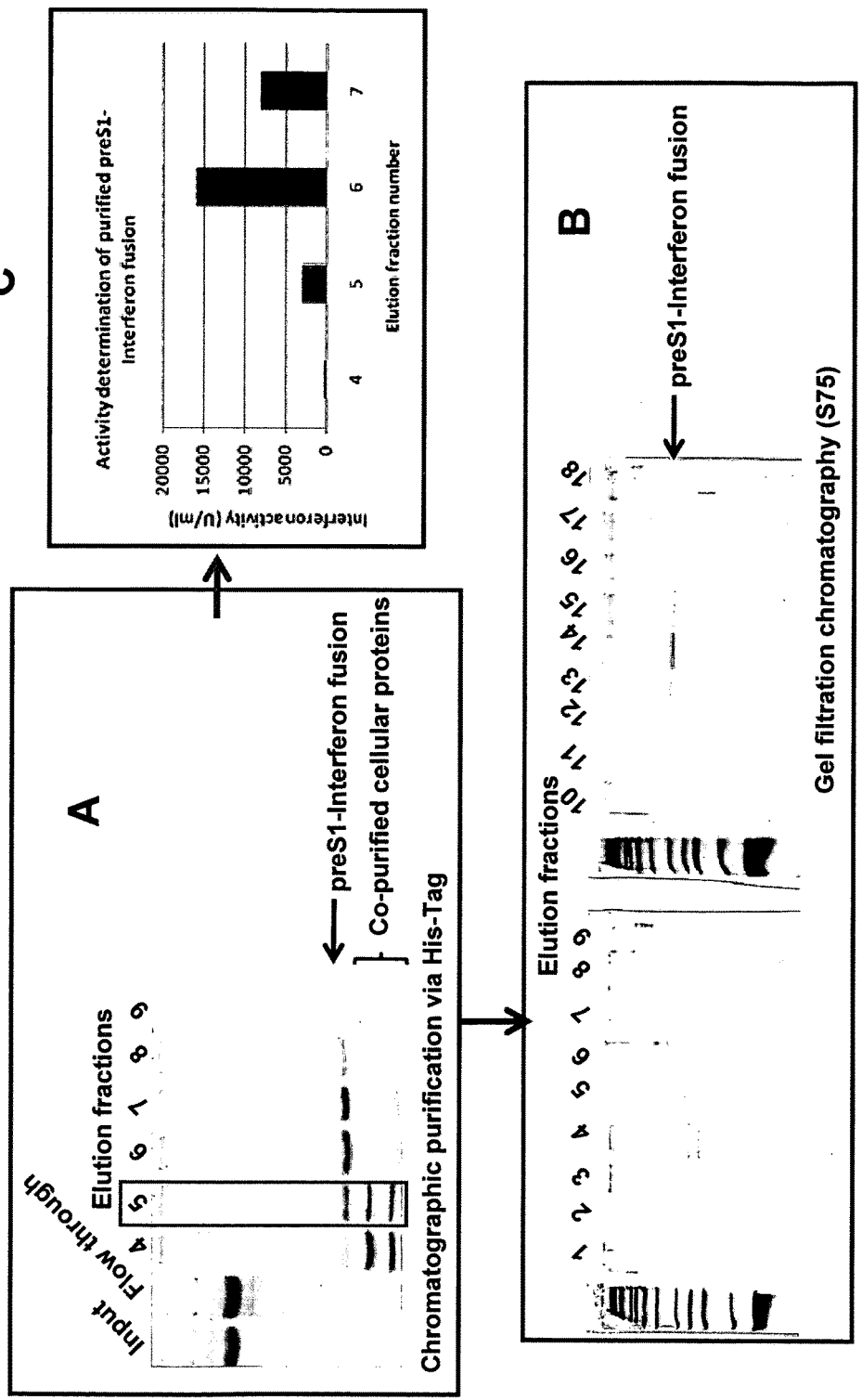

FIG. 15. Purification and activity test of HBVpreS/2-20$^{myr}$(D)-IFNalpha
Purification of the fusion protein HBVpreS/2-20$^{myr}$(D)-mouse Interferon alpha 2 from the supernatant of insect cells, which were infected with a recombinant baculovirus.
A First chromatography step: chromatographic purification via His-Tag, using Ni-agarose, because the HBVpreS/2-20$^{myr}$(D)-IFNalpha construct carries a C-terminal His-tag.
B Second chromatography step: gel filtration chromatography (S75)
C The elution fractions of the first chromatography step were tested for IFN.
See also Examples.
For the amino acid sequence of HBVpreS/2-20(D) see SEQ ID NO. 38.

EXAMPLES

Synthesis of the Hydrophobic Modified preS-Derived Peptides
The synthesis was carried out as described e.g. in (10).
Biodistribution of the Hydrophobic Modified preS-Derived Peptides
The biodistribution of the hydrophobic modified preS-derived peptides was studied in male NMRI mice. All experiments were performed in compliance with German laws. The peptides, containing an additional Tyr-residue at the C-terminal end were labelled with $^{131}$I (Amersham Biosciences, Freiburg, Germany) by the chloramine-T method and purified by HPLC. The labelled peptides were subcutaneously administered by injection of a solution in 50% DMSO. At selected times mice were sacrificed and the radioactivity contained in the blood, heart, lung, spleen, liver, kidney, muscle and brain was measured in a γ-counter (Canberra Packard, Rüsselsheim, Germany) and expressed as a percentage of injected dose per gram of tissue (% ID/g).
Stability Assessment of the Hydrophobic Modified preS-Derived Peptides after Extraction from the Liver To determine the peptide stability in the liver 131I labelled HBVpreS/2-48$^{myr}$ (D) was extracted from one liver lobe 24 h post subcutaneous injection. To that aim, 1 ml water per gram frozen liver tissue was added to the sample. After homogenization an equal volume of acetonitrile was added and the homogenization was repeated. After centrifugation (2×10 min at 4000×g) this solution was separated on a reverse phase HPLC column and the radioactivity of each fraction was quantified in a gamma counter.

Cell Lines and Primary Cell Cultures.

HepaRG cells were grown in William's E medium supplemented with 10% fetal calf serum (FCS), 100 units/ml penicillin, 100 µg/ml streptomycin, 5 µg/ml insulin and 5×10$^{-5}$ M hydrocortisone hemisuccinate (10). Cells were passaged 1/5 every two weeks by trypsination. Two to three weeks before infection cell differentiation was induced by adding 2% DMSO into the maintenance medium. The medium was exchanged every 2-3 days.

Infection Competition Assays.

As an infectious inoculum, a 50-fold concentrated culture supernatant of HepG2 clone 2.2.15 (11) cells was used, because of an unlimited supply and a constant quality. It was prepared from freshly collected supernatants by precipitating viral particles in the presence of 6% polyethylene glycol (PEG) 8000. The pellet was resuspended in phosphate buffered saline (PBS) containing 25% FCS. Aliquots were stored at −80° C. Differentiated HepaRG cells or PHH were incubated with the concentrated infectious source, 10-fold diluted in culture medium supplemented with 4% PEG 8000 (Sigma), for 20 h at 37° C. At the end of the incubation, cells were washed three times with the culture medium and maintained in the presence of 2% DMSO and 5×10$^{-5}$ M hydrocortisone hemisuccinate and harvested at indicated times.

Competition experiments were performed in 12-well plates. Approximately 1×10$^6$ cells were first pre-incubated for 30 min with chemically synthesized HBV derived peptides followed by a co-incubation of cells with peptide and virus for 20 h. All competition series were performed at least twice and the results of one representative experiment are shown in each case (see FIGS. 3 to 7).

HepaRG cells were infected either in absence (0 nM) or in the presence of 1, 5, 25, 100 and 2000 nM of the respective peptides of the invention. The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Immunofluorescence Experiments/Microscopy

Primary hepatocytes grown on cover slips were incubated with the respective peptide at 200 nM in serum-free cell culture medium. After 1 hour incubation at 37° C. cells were fixed and nuclei were stained with DAPI. Fluorescence microscopy was performed on a Spinning Disk Confocal Microscope at 600× magnification.

FACS Analysis

Cryo-preserved primary hepatocytes were thawed and washed with serum-free medium. In each reaction 4×10$^5$ cells/ml were incubated with the respective peptide at a concentration of 200 nM in serum-free cell culture medium. The staining was performed for 30 minutes at room temperature with frequent mixing. Subsequently, cells were washed extensively and resuspended in PBS to proceed with the FACS analysis.

Results are shown in the Figures.

Fusion Constructs of HBVpreS1-Peptides with Mouse Interferon Alpha-Production, Purification and Activity Test HBVpreS1-peptide-mouse interferon alpha fusion proteins (see FIG. 14) were expressed in Hi5-insect cells using the baculovirus expression system. The fusion proteins secreted in the cell supernatants were harvested on day 5 post infection and purified in a first step by an affinity chromatography for the His-tag fused C-terminally to the preS1-interferon. The activity of the preS1-interferon proteins in the elution fractions was measured by their ability to inhibit Newcastle disease virus mediated cell death. The elution fractions containing functional preS1-interferon proteins were further purified by gel filtration chromatography on a S75-sepharose column with a 1M urea-PBS buffer (see FIG. 15).

The features disclosed in the foregoing description, in the claims and/or in the accompanying drawings may, both separately and in any combination thereof, be material for realizing the invention in diverse forms thereof.

REFERENCES

1. Seeger, C. & Mason, W. S. Hepatitis B virus biology. *Microbiol. Mol Biol Rev* 64, 51-68 (2000).
2. Nassal, M. Hepatitis B virus morphogenesis. *Curr Top Microbiol Immunol* 214, 297-337 (1996).
3. Gripon, P., Le Seyec, J., Rumin, S. & Guguen-Guillouzo, C. Myristylation of the hepatitis B virus large surface protein is essential for viral infectivity. *Virology* 213, 292-299 (1995).
4. Le Seyec, J., Chouteau, P., Cannie, I., Guguen-Guillouzo, C. & Gripon, P. Infection process of the hepatitis B virus depends on the presence of a defined sequence in the preS1 domain. *J Virol* 73, 2052-2057 (1999).
5. Juliano R L (1988) Factors affecting the clearance kinetics and tissue distribution of liposomes, microspheres, and emulsions. *Adv Drug Deliv Rev* 2:31-54.
6. Hashida M and Takakura Y (1994) Pharmacokinetics in design of polymeric drug delivery systems. *J Control Release* 31: 163-171.
7. Lu, X. M., Fischman, A. J., Jyawook, S. L., Hendricks, K., Tompkins, R. G. and Yarmush, M. L. (1994) Antisense DNA delivery in vivo: liver targeting by receptor-mediated uptake. *J. Nucl. Med.* 35, 269-275.
8. Freireich, E. J., Gehan, E. A., Rall, D. P., Schmidt, L. H. & Skipper, H. E. Quantitative comparison of toxicity of anticancer agents in mouse, rat, hamster, dog, monkey, and man. *Cancer Chemother Rep* 50, 219-244 (1966).
9. Erion, M. D. Prodrugs for liver-targeted drug delivery. 541-572. Biotechnology: Pharmaceutical Aspects. Volume V, Part II, Prodrugs. Springer New York, 2007.
10. Gripon, P., Cannie, I. & Urban, S. Efficient inhibition of hepatitis B virus infection by acylated peptides derived from the large viral surface protein. *J Virol* 79, 1613-1622 (2005).
11. Glebe D, Urban S, Knoop E V, Cag N, Krass P, Grun S, Bulavaite A, Sasnauskas K, Gerlich W H. Mapping of the hepatitis B virus attachment site by use of infection-inhibiting preS1 lipopeptides and tupaia hepatocytes. *Gastroenterology* 129, 234-245 (2005).

The invention claimed is:

1. A hydrophobic modified preS-derived peptide of hepatitis B virus (HBV) of the formula $$[H_m\text{-}P\text{-}R_n]A_o$$

wherein
P is a preS-derived peptide consisting of:
  a) an N-terminally and/or C-terminally truncated variant of HBV preS consensus sequence as shown in SEQ ID NO: 1, wherein the truncated variant consists of a minimum of 10 and a maximum of 46 amino acids; or
  b) a truncated variant of HBV preS consensus sequence as shown in SEQ ID NO: 1, wherein the truncated variant consists of a minimum of 7 and a maximum of 46 amino acids, and wherein the truncated variant comprises the sequence of SEQ ID NO: 21;
wherein,
H is an acylation of the preS-derived peptide P that is N-terminal of P,
m is at least 1;
R is a C-terminal modification of said preS-derived peptide P, which is a moiety that protects from degradation, selected from amides, albumin, natural polymers, and synthetic polymers;
n is 0 or at least 1;
A is an anchor group, selected from ester, ether, disulfide, amide, thiol, and thioester; and
o is 0 or at least 1;
  wherein said hydrophobic modified peptide further comprises at least one compound selected from drugs; prodrugs; labels; recombinant viruses or derivatives thereof; carriers or depots for a drug, prodrugs or labels; and immunogenic epitopes; wherein the label is a contrast agent; and wherein the compound and the hydrophobic peptide form a conjugate.

2. The hydrophobic modified preS-derived peptide according to claim 1, wherein the acylation is selected from acylation with myristoyl (C 14), palmitoyl (C 16) or stearoyl (C 18).

3. The hydrophobic modified preS-derived peptide according to claim 1, wherein H and/or R is linked to P via a linker or spacer.

4. The hydrophobic modified preS-derived peptide according to claim 1, wherein P consists of N-terminally and/or C-terminally truncated variants of a minimum of 20 and a maximum of 46 consecutive amino acids of SEQ ID NO: 1.

5. The hydrophobic modified preS-derived peptide according to claim 1, wherein P consists of the N-terminally and/or C-terminally truncated variants of a maximum of 46 consecutive amino acids of SEQ ID NO: 1 and comprises an amino acid sequence selected from amino acid residues 2 to 21, residues 2 to 20, or residues 9 to 15 of the HBV preS consensus sequence as shown in SEQ ID NO: 1.

6. The hydrophobic modified preS-derived peptide according to claim 1, wherein P does not comprise amino acid substitutions and/or deletions at residues 9 to 15 of SEQ ID NO: 1.

7. The hydrophobic modified preS-derived peptide according to claim 1, wherein P consists of the N-terminally and/or C-terminally truncated variants of a maximum of 46 consecutive amino acids of SEQ ID NO: 1 and comprises an amino acid sequence of SEQ ID NO: 38.

8. The hydrophobic modified preS-derived peptide according to claim 1, wherein P comprises an amino acid sequence selected from SEQ ID NOs: 31 to 37 and variants thereof.

9. The hydrophobic modified preS-derived peptide according to claim 1, wherein P comprises an amino acid sequence selected from SEQ ID NO: 11, SEQ ID NO: 12, SEQ ID NO: 13, SEQ ID NO: 16, SEQ ID NO: 23, SEQ ID NO: 26, SEQ ID NO: 31, and SEQ ID NO: 38.

10. The hydrophobic modified preS-derived peptide according to claim 1, wherein the acylation is selected from acylation with stearoyl (C 18) or acylation with myristoyl (C 14).

11. A pharmaceutical composition comprising; at least one hydrophobic modified preS-derived peptide of HBV according to claim 1, and at least one compound to be specifically delivered to the liver; wherein the compound may be conjugated to the peptide; and, optionally, a pharmaceutically acceptable carrier and/or excipient.

12. A method for the identification of a HBV receptor, comprising the use of at least one hydrophobic modified preS-derived peptide of HBV according to claim 1, and at least one compound to be specifically delivered to the liver, wherein the compound is conjugated to the peptide; and, optionally, a pharmaceutically acceptable carrier and/or excipient.

13. The hydrophobic modified preS-derived peptide according to claim 1, wherein the compound is selected from interferons;
  viral reverse transcriptase inhibitors;
  viral RNA polymerase inhibitors;
  viral core assembly inhibitors or viral nucleocapsid inhibitors;
  kinase inhibitors;
  nucleoside analogues;
  protease inhibitors;
  proteasom inhibitors;
  antibodies or fragments thereof;
  siRNA or precursors thereof;
  farnesylation inhibitors;
  alcohol dehydrogenase (ADH) or an activator thereof;
  cholesterol biosynthesis inhibitors;
  inhibitors of the liver stage of a virus or a non-viral pathogen; and
  antibiotics.

14. The hydrophobic modified preS-derived peptide according to claim 13, wherein the drug is in the form of a prodrug.

15. The hydrophobic modified preS-derived peptide according to claim 13, wherein the compound is interferon and is attached to a peptide consisting of the N-terminally and/or C-terminally truncated variants of a maximum of 46 consecutive amino acids of SEQ ID NO: 1 and that comprises an amino acid sequence of SEQ ID NO: 38.

16. The hydrophobic modified preS-derived peptide according to claim 15, wherein H is a hydrophobic modification by acylation.

17. The hydrophobic modified preS-derived peptide according to claim 1, wherein the conjugate is formed by covalent attachment or by complex formation.

18. The hydrophobic modified preS-derived peptide according to claim 17, wherein the conjugate is formed by covalently attaching a compound to an anchor group A.

19. The hydrophobic modified preS-derived peptide according to claim 18, wherein the anchor group A further comprises a spacer or linker.

20. The hydrophobic modified preS-derived peptide according to claim 19, wherein the spacer or linker comprises a recognition site, which is recognized by a liver protein.

* * * * *

SEQUENCE LISTING

<160> NUMBER OF SEQ ID NOS: 42

<210> SEQ ID NO 1
<211> LENGTH: 59
<212> TYPE: PRT
<213> ORGANISM: Artificial
<220> FEATURE:
<223> OTHER INFORMATION: HBV preS1 consensus sequence (positions (-11) to 48)

<400> SEQUENCE: 1

Met Gly Gly Trp Ser Ser Thr Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Arg Ala Asn Ser Asn Asn Pro Asp Trp Asp Phe Asn Pro Asn
        35                  40                  45

Lys Asp His Trp Pro Glu Ala Asn Lys Val Gly
    50                  55

<210> SEQ ID NO 2
<211> LENGTH: 59
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly
    50                  55

<210> SEQ ID NO 3
<211> LENGTH: 59
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala Asn Lys Val Gly
    50                  55

<210> SEQ ID NO 4
<211> LENGTH: 59
<212> TYPE: PRT
<213> ORGANISM: Artificial
<220> FEATURE:
<223> OTHER INFORMATION: HBV preS1 sequence positions (-11) to 48, corresponding to HBV genotype C, but Q46K

<400> SEQUENCE: 4

Met Gly Gly Trp Ser Ser Lys Pro Arg Gln Gly Met Gly Thr Asn Leu
1               5                   10                  15

-continued

```
Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Lys Val Gly
    50                  55

<210> SEQ ID NO 5
<211> LENGTH: 48
<212> TYPE: PRT
<213> ORGANISM: Hepatitis B virus

<400> SEQUENCE: 5

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

<210> SEQ ID NO 6
<211> LENGTH: 58
<212> TYPE: PRT
<213> ORGANISM: Hepatitis B virus

<400> SEQUENCE: 6

Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly
    50                  55

<210> SEQ ID NO 7
<211> LENGTH: 59
<212> TYPE: PRT
<213> ORGANISM: Hepatitis B virus

<400> SEQUENCE: 7

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly
    50                  55

<210> SEQ ID NO 8
<211> LENGTH: 58
<212> TYPE: PRT
<213> ORGANISM: Hepatitis B virus

<400> SEQUENCE: 8

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30
```

Phe Arg Ala Asn Thr Asn Asn Pro Asp Trp Asp Phe Asn Pro Lys Lys
            35                  40                  45

Asp Pro Trp Pro Glu Ala Asn Lys Val Gly
    50                  55

<210> SEQ ID NO 9
<211> LENGTH: 59
<212> TYPE: PRT
<213> ORGANISM: Hepatitis B virus

<400> SEQUENCE: 9

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
                20                  25                  30

Leu Phe Arg Ala Asn Ser Ser Ser Pro Asp Trp Asp Phe Asn Thr Asn
            35                  40                  45

Lys Asp Asn Trp Pro Met Ala Asn Lys Val Gly
    50                  55

<210> SEQ ID NO 10
<211> LENGTH: 48
<212> TYPE: PRT
<213> ORGANISM: Woolly Monkey Hepatitis B virus

<400> SEQUENCE: 10

Met Gly Leu Asn Gln Ser Thr Phe Asn Pro Leu Gly Phe Phe Pro Ser
1               5                   10                  15

His Gln Leu Asp Pro Leu Phe Lys Ala Asn Ala Gly Ser Ala Asp Trp
                20                  25                  30

Asp Lys Asn Pro Asn Lys Asp Pro Trp Pro Gln Ala His Asp Thr Ala
            35                  40                  45

<210> SEQ ID NO 11
<211> LENGTH: 47
<212> TYPE: PRT
<213> ORGANISM: Artificial
<220> FEATURE:
<223> OTHER INFORMATION: HBV preS1 consensus sequence (positions 2 to
      48)

<400> SEQUENCE: 11

Gly Thr Asn Leu Ser Val Pro Asn Pro Leu Gly Phe Phe Pro Asp His
1               5                   10                  15

Gln Leu Asp Pro Ala Phe Arg Ala Asn Ser Asn Pro Asp Trp Asp
                20                  25                  30

Phe Asn Pro Asn Lys Asp His Trp Pro Glu Ala Asn Lys Val Gly
            35                  40                  45

<210> SEQ ID NO 12
<211> LENGTH: 20
<212> TYPE: PRT
<213> ORGANISM: Artificial
<220> FEATURE:
<223> OTHER INFORMATION: HBV preS1 consensus sequence (positions 2 to
      21)

<400> SEQUENCE: 12

Gly Thr Asn Leu Ser Val Pro Asn Pro Leu Gly Phe Phe Pro Asp His
1               5                   10                  15

Gln Leu Asp Pro

20

<210> SEQ ID NO 13
<211> LENGTH: 47
<212> TYPE: PRT
<213> ORGANISM: Artificial
<220> FEATURE:
<223> OTHER INFORMATION: HBV preS1 sequence positions 2 to 48,
      corresponding to HBV genotype C, but Q46K

<400> SEQUENCE: 13

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 14
<211> LENGTH: 44
<212> TYPE: PRT
<213> ORGANISM: Artificial
<220> FEATURE:
<223> OTHER INFORMATION: HBV preS1 sequence positions 5 to 48,
      corresponding to HBV genotype C, but Q46K

<400> SEQUENCE: 14

Leu Ser Val Pro Asn Pro Leu Gly Phe Phe Pro Asp His Gln Leu Asp
1               5                   10                  15

Pro Ala Phe Gly Ala Asn Ser Asn Asn Pro Asp Trp Asp Phe Asn Pro
            20                  25                  30

Asn Lys Asp His Trp Pro Glu Ala Asn Lys Val Gly
        35                  40

<210> SEQ ID NO 15
<211> LENGTH: 40
<212> TYPE: PRT
<213> ORGANISM: Artificial
<220> FEATURE:
<223> OTHER INFORMATION: HBV preS1 sequence positions 9 to 48,
      corresponding to HBV genotype C, but Q46K

<400> SEQUENCE: 15

Asn Pro Leu Gly Phe Phe Pro Asp His Gln Leu Asp Pro Ala Phe Gly
1               5                   10                  15

Ala Asn Ser Asn Asn Pro Asp Trp Asp Phe Asn Pro Asn Lys Asp His
            20                  25                  30

Trp Pro Glu Ala Asn Lys Val Gly
        35                  40

<210> SEQ ID NO 16
<211> LENGTH: 20
<212> TYPE: PRT
<213> ORGANISM: Hepatitis B virus (positions 2 to 21, genotype C)

<400> SEQUENCE: 16

Gly Thr Asn Leu Ser Val Pro Asn Pro Leu Gly Phe Phe Pro Asp His
1               5                   10                  15

Gln Leu Asp Pro
            20

<210> SEQ ID NO 17
<211> LENGTH: 17

```
<212> TYPE: PRT
<213> ORGANISM: Hepatitis B virus (positions 5 to 21, genotype C)

<400> SEQUENCE: 17

Leu Ser Val Pro Asn Pro Leu Gly Phe Phe Pro Asp His Gln Leu Asp
1               5                   10                  15
Pro

<210> SEQ ID NO 18
<211> LENGTH: 13
<212> TYPE: PRT
<213> ORGANISM: Hepatitis B virus (positions 9 to 21, genotype C)

<400> SEQUENCE: 18

Asn Pro Leu Gly Phe Phe Pro Asp His Gln Leu Asp Pro
1               5                   10

<210> SEQ ID NO 19
<211> LENGTH: 14
<212> TYPE: PRT
<213> ORGANISM: Hepatitis B virus (positions 2 to 15, genotype C)

<400> SEQUENCE: 19

Gly Thr Asn Leu Ser Val Pro Asn Pro Leu Gly Phe Phe Pro
1               5                   10

<210> SEQ ID NO 20
<211> LENGTH: 11
<212> TYPE: PRT
<213> ORGANISM: Hepatitis B virus (positions 5 to 15, genotype C)

<400> SEQUENCE: 20

Leu Ser Val Pro Asn Pro Leu Gly Phe Phe Pro
1               5                   10

<210> SEQ ID NO 21
<211> LENGTH: 7
<212> TYPE: PRT
<213> ORGANISM: Hepatitis B virus (positions 9 to 15)

<400> SEQUENCE: 21

Asn Pro Leu Gly Phe Phe Pro
1               5

<210> SEQ ID NO 22
<211> LENGTH: 22
<212> TYPE: PRT
<213> ORGANISM: Hepatitis B virus (positions (-2) to 20, genotype C)

<400> SEQUENCE: 22

Gln Gly Met Gly Thr Asn Leu Ser Val Pro Asn Pro Leu Gly Phe Phe
1               5                   10                  15
Pro Asp His Gln Leu Asp
            20

<210> SEQ ID NO 23
<211> LENGTH: 47
<212> TYPE: PRT
<213> ORGANISM: Hepatitis B virus (positions 2 to 48, genotype D)

<400> SEQUENCE: 23

Gly Gln Asn Leu Ser Thr Ser Asn Pro Leu Gly Phe Phe Pro Asp His
1               5                   10                  15
```

```
Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 24
<211> LENGTH: 44
<212> TYPE: PRT
<213> ORGANISM: Hepatitis B virus (positions 5 to 48, genotype D)

<400> SEQUENCE: 24

Leu Ser Thr Ser Asn Pro Leu Gly Phe Phe Pro Asp His Gln Leu Asp
1               5                   10                  15

Pro Ala Phe Arg Ala Asn Thr Ala Asn Pro Asp Trp Asp Phe Asn Pro
            20                  25                  30

Asn Lys Asp Thr Trp Pro Asp Ala Asn Lys Val Gly
        35                  40

<210> SEQ ID NO 25
<211> LENGTH: 40
<212> TYPE: PRT
<213> ORGANISM: Hepatitis B virus (positions 9 to 48, genotype D)

<400> SEQUENCE: 25

Asn Pro Leu Gly Phe Phe Pro Asp His Gln Leu Asp Pro Ala Phe Arg
1               5                   10                  15

Ala Asn Thr Ala Asn Pro Asp Trp Asp Phe Asn Pro Asn Lys Asp Thr
            20                  25                  30

Trp Pro Asp Ala Asn Lys Val Gly
        35                  40

<210> SEQ ID NO 26
<211> LENGTH: 20
<212> TYPE: PRT
<213> ORGANISM: Hepatitis B virus (positions 2 to 21, genotype D)

<400> SEQUENCE: 26

Gly Gln Asn Leu Ser Thr Ser Asn Pro Leu Gly Phe Phe Pro Asp His
1               5                   10                  15

Gln Leu Asp Pro
            20

<210> SEQ ID NO 27
<211> LENGTH: 17
<212> TYPE: PRT
<213> ORGANISM: Hepatitis B virus (positions 5 to 21, genotype D)

<400> SEQUENCE: 27

Leu Ser Thr Ser Asn Pro Leu Gly Phe Phe Pro Asp His Gln Leu Asp
1               5                   10                  15

Pro

<210> SEQ ID NO 28
<211> LENGTH: 13
<212> TYPE: PRT
<213> ORGANISM: Hepatitis B virus (positions 9 to 21, genotype D)

<400> SEQUENCE: 28

Asn Pro Leu Gly Phe Phe Pro Asp His Gln Leu Asp Pro
1               5                   10
```

```
<210> SEQ ID NO 29
<211> LENGTH: 14
<212> TYPE: PRT
<213> ORGANISM: Hepatitis B virus (positions 2 to 15, genotype D)

<400> SEQUENCE: 29

Gly Gln Asn Leu Ser Thr Ser Asn Pro Leu Gly Phe Phe Pro
1               5                   10

<210> SEQ ID NO 30
<211> LENGTH: 11
<212> TYPE: PRT
<213> ORGANISM: Hepatitis B virus (positions 5 to 15, genotype D)

<400> SEQUENCE: 30

Leu Ser Thr Ser Asn Pro Leu Gly Phe Phe Pro
1               5                   10

<210> SEQ ID NO 31
<211> LENGTH: 47
<212> TYPE: PRT
<213> ORGANISM: Artificial
<220> FEATURE:
<223> OTHER INFORMATION: HBV preS1 sequence positions 2 to 48,
      corresponding to genoytpe C (but Q46K), with Ala substitution in
      positions 21, 23, 29, 30

<400> SEQUENCE: 31

Gly Thr Asn Leu Ser Val Pro Asn Pro Leu Gly Phe Phe Pro Asp His
1               5                   10                  15

Gln Leu Asp Ala Ala Ala Gly Ala Asn Ser Asn Ala Ala Asp Trp Asp
            20                  25                  30

Phe Asn Pro Asn Lys Asp His Trp Pro Glu Ala Asn Lys Val Gly
        35                  40                  45

<210> SEQ ID NO 32
<211> LENGTH: 59
<212> TYPE: PRT
<213> ORGANISM: Artificial
<220> FEATURE:
<223> OTHER INFORMATION: HBV preS1 sequence positions (-11) to 48,
      corresponding to genoytpe C (but Q46K), D20A

<400> SEQUENCE: 32

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Ala Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Lys Val Gly
        50                  55

<210> SEQ ID NO 33
<211> LENGTH: 47
<212> TYPE: PRT
<213> ORGANISM: Artificial
<220> FEATURE:
<223> OTHER INFORMATION: HBV preS1 sequence positions 2 to 48,
      corresponding to genoytpe C (but Q46K), D20A

<400> SEQUENCE: 33

Gly Thr Asn Leu Ser Val Pro Asn Pro Leu Gly Phe Phe Pro Asp His
1               5                   10                  15
```

Gln Leu Ala Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 34
<211> LENGTH: 59
<212> TYPE: PRT
<213> ORGANISM: Artificial
<220> FEATURE:
<223> OTHER INFORMATION: HBV preS1 sequence positions (-11) to 48,
      corresponding to genoytpe C (but Q46K), S27A, N29A

<400> SEQUENCE: 34

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ala Asn Ala Pro Asp Trp Asp Phe Asn Pro Asn
        35                  40                  45

Lys Asp His Trp Pro Glu Ala Asn Lys Val Gly
    50                  55

<210> SEQ ID NO 35
<211> LENGTH: 47
<212> TYPE: PRT
<213> ORGANISM: Artificial
<220> FEATURE:
<223> OTHER INFORMATION: HBV preS1 sequence positions 2 to 48,
      corresponding to genoytpe C (but Q46K), S27A, N29A

<400> SEQUENCE: 35

Gly Thr Asn Leu Ser Val Pro Asn Pro Leu Gly Phe Phe Pro Asp His
1               5                   10                  15

Gln Leu Asp Pro Ala Phe Gly Ala Asn Ala Asn Ala Pro Asp Trp Asp
            20                  25                  30

Phe Asn Pro Asn Lys Asp His Trp Pro Glu Ala Asn Lys Val Gly
        35                  40                  45

<210> SEQ ID NO 36
<211> LENGTH: 59
<212> TYPE: PRT
<213> ORGANISM: Artificial
<220> FEATURE:
<223> OTHER INFORMATION: HBV preS1 sequence positions (-11) to 48,
      corresponding to genoytpe C (but Q46K), D20A, S27A, N29A

<400> SEQUENCE: 36

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Ala Pro
            20                  25                  30

Ala Phe Gly Ala Asn Ala Asn Ala Pro Asp Trp Asp Phe Asn Pro Asn
        35                  40                  45

Lys Asp His Trp Pro Glu Ala Asn Lys Val Gly
    50                  55

<210> SEQ ID NO 37
<211> LENGTH: 47
<212> TYPE: PRT
<213> ORGANISM: Artificial
<220> FEATURE:
<223> OTHER INFORMATION: HBV preS1 sequence positions 2 to 48, -continued corresponding to genoytpe C (but Q46K), D20A, S27A, N29A

<400> SEQUENCE: 37

Gly Thr Asn Leu Ser Val Pro Asn Pro Leu Gly Phe Phe Pro Asp His
1               5                   10                  15

Gln Leu Ala Pro Ala Phe Gly Ala Asn Ala Asn Ala Pro Asp Trp Asp
            20                  25                  30

Phe Asn Pro Asn Lys Asp His Trp Pro Glu Ala Asn Lys Val Gly
        35                  40                  45

<210> SEQ ID NO 38
<211> LENGTH: 19
<212> TYPE: PRT
<213> ORGANISM: Hepatitis B virus (positions 2 to 20, genotype D)

<400> SEQUENCE: 38

Gly Thr Asn Leu Ser Val Pro Asn Pro Leu Gly Phe Phe Pro Asp His
1               5                   10                  15

Gln Leu Asp

<210> SEQ ID NO 39
<211> LENGTH: 48
<212> TYPE: PRT
<213> ORGANISM: Artificial
<220> FEATURE:
<223> OTHER INFORMATION: HBV preS1 sequence positions 2 to 48, genotype
      C, plus K in position 49

<400> SEQUENCE: 39

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly Lys
        35                  40                  45

<210> SEQ ID NO 40
<211> LENGTH: 48
<212> TYPE: PRT
<213> ORGANISM: Artificial
<220> FEATURE:
<223> OTHER INFORMATION: HBV preS1 sequence positions 2 to 48, genotype
      C, plus K in position 49, positions L11 and F13 are D-amino acids

<400> SEQUENCE: 40

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly Lys
        35                  40                  45

<210> SEQ ID NO 41
<211> LENGTH: 48
<212> TYPE: PRT
<213> ORGANISM: Artificial
<220> FEATURE:
<223> OTHER INFORMATION: HBV preS1 sequence positions 2 to 48,
      corresponding to genotype C (but Q46K), plus K in position 49

<400> SEQUENCE: 41

Gly Thr Asn Leu Ser Val Pro Asn Pro Leu Gly Phe Phe Pro Asp His
1               5                   10                  15

```
Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly Lys
        35                  40                  45

<210> SEQ ID NO 42
<211> LENGTH: 48
<212> TYPE: PRT
<213> ORGANISM: Artificial
<220> FEATURE:
<223> OTHER INFORMATION: HBV preS1 sequence positions 2 to 48,
      corresponding to genotype C (but Q46K), plus K in position 49,
      positions L11 and F13 are D-amino acids

<400> SEQUENCE: 42

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly Lys
        35                  40                  45
```